US012040083B2

(12) United States Patent
Mohtar et al.

(10) Patent No.: US 12,040,083 B2
(45) Date of Patent: Jul. 16, 2024

(54) MACHINE LEARNING APPLICATIONS FOR IMPROVING MEDICAL OUTCOMES AND COMPLIANCE

(71) Applicant: Texas Medical Center, Houston, TX (US)

(72) Inventors: Omar Mohtar, Houston, TX (US); Vibhav Jha, Dover, NH (US)

(73) Assignee: Texas Medical Center, Houston, TX (US)

( * ) Notice: Subject to any disclaimer, the term of this patent is extended or adjusted under 35 U.S.C. 154(b) by 0 days.

(21) Appl. No.: 18/361,494

(22) Filed: Jul. 28, 2023

(65) Prior Publication Data

US 2024/0038375 A1 Feb. 1, 2024

Related U.S. Application Data

(60) Provisional application No. 63/369,903, filed on Jul. 29, 2022.

(51) Int. Cl.
*G16H 40/20* (2018.01)
*G06F 21/62* (2013.01)
*G06F 40/174* (2020.01)
*G16H 10/60* (2018.01)

(52) U.S. Cl.
CPC ......... *G16H 40/20* (2018.01); *G06F 21/6254* (2013.01); *G06F 40/174* (2020.01); *G16H 10/60* (2018.01)

(58) Field of Classification Search
CPC ...... G16H 40/20; G16H 10/60; G06F 40/174; G06F 21/6254
See application file for complete search history.

(56) References Cited

U.S. PATENT DOCUMENTS

| 2012/0329015 | A1* | 12/2012 | Thesman | G16H 70/20 |
| | | | | 707/812 |
| 2016/0147945 | A1* | 5/2016 | MacCarthy | H04W 12/02 |
| | | | | 705/51 |
| 2018/0261330 | A1* | 9/2018 | Saripalli | G06N 20/00 |
| 2019/0371438 | A1* | 12/2019 | Chintamaneni | G10L 15/26 |
| 2021/0117804 | A1* | 4/2021 | Koehler | G06N 3/084 |
| 2021/0398676 | A1* | 12/2021 | Evans | G06N 3/08 |
| 2021/0406716 | A1* | 12/2021 | Broyles | G06F 40/174 |
| 2022/0277841 | A1* | 9/2022 | Harmon | G16H 10/60 |

(Continued)

*Primary Examiner* — Fonya M Long
*Assistant Examiner* — Anthony Balaj
(74) *Attorney, Agent, or Firm* — Goodwin Procter LLP

(57) ABSTRACT

Disclosed herein are methods for intelligently populating medical compliance forms (MCFs) with at least patient data to meet compliance requirements (e.g., meeting patient data compliance requirements such as HIPAA requirements, as well as compliance requirements concerning patient forms). In particular, methods involve training and deploying machine learning models that can appropriately analyze a wide array of MCFs with varying formats. Advantages of the methods disclosed herein are three-fold: 1) reducing the amount of time and resources that a healthcare provider needs to commit to satisfying compliance requirements and 2) improving patient outcome by more intelligently incorporating data in medical compliance forms, and 3) ensuring meeting of compliance requirements (e.g., HIPAA compliance requirements).

20 Claims, 10 Drawing Sheets

(56) References Cited

U.S. PATENT DOCUMENTS

2023/0069182 A1\* 3/2023 Peresie .................. G16H 10/60
2023/0282322 A1\* 9/2023 Rajkumar .............. G16H 10/60
705/3

\* cited by examiner

MACHINE LEARNING APPLICATIONS FOR IMPROVING MEDICAL OUTCOMES AND COMPLIANCE

CROSS-REFERENCE TO RELATED APPLICATIONS

This application claims priority to and the benefit of U.S. Provisional App. No. 63/369,903, filed Jul. 29, 2022, and titled "MACHINE LEARNING APPLICATIONS FOR IMPROVING MEDICAL OUTCOMES AND COMPLIANCE" which is incorporated herein in its entirety.

BACKGROUND

Completing non-clinical tasks in healthcare entails moving parts that providers can no longer keep up with. Imposed on providers are ever-increasing compliance requirements such as requirements of timely recording patient notes and accurately capturing medical documentation (e.g., for medical compliance forms). These requirements are cumbersome and represent additional responsibilities for healthcare providers on top of the medical care that they provide to their patients. One example of a medical compliance form is a patient assessment form (PAF) which requires on average 90 minutes for a provider to complete per patient. Thus providers need to either spend hours inputting information on the electronic medical records (EMR), or they need to hire additional staff to complete non-clinical tasks. As a result, given the cumbersome nature of these compliance requirements, providers may altogether forego meeting these compliance requirements, which leads to poor patient outcome (e.g., due to poor documentation and poor patient treatment).

SUMMARY

Disclosed herein are methods for improved handling and preparation of medical compliance forms. In various embodiments, methods disclosed herein involve deployment of trained machine learning models that identify relevant patient data that is to be incorporated into the fields of medical compliance forms. In various embodiments, methods disclosed herein involve trained machine learning models that can intelligently identify data to be included in medical compliance forms. These machine learning models can intelligently identify data to be included in medical compliance forms that may lead to improved healthcare outcomes in comparison to the tasks healthcare providers perform currently. Furthermore, while methods disclosed herein involve analyzing and populating medical compliance forms, these methods further ensure that patient data is handled in accordance with compliance requirements. For example, to ensure HIPAA compliance, machine learning models are only exposed to de-identified patient data and do not have access to the actual patient identity. Patient data is only stored on-premise to deter data leaks. Thus, advantages of the method disclosed herein are three-fold: 1) reducing the amount of time and resources that a healthcare provider needs to commit to satisfying compliance requirements and 2) improving patient outcome by more intelligently incorporating data in medical compliance forms, and 3) ensuring meeting of compliance requirements (e.g., HIPAA compliance requirements).

Disclosed herein is a method for improving medical compliance, the method comprising: obtaining an unfilled medical compliance form (MCF); identifying one or more fields for populating health data of a patient, the patient associated with a patient identifier; transmitting the patient identifier to an entity, wherein the entity has access to the patient identifier, an identity of the patient, and corresponding patient data of the patient; receiving, from the entity, the corresponding patient data of the patient without receiving the identity of the patient; deploying a predictive model to analyze the one or more fields, wherein the predictive model outputs decisions that identify subsets of the patient data to be included in the one or more fields; populating the one or more fields of the unfilled MCF with the identified subsets of the patient data to generate a populated MCF for the patient; and providing the populated MCF. In various embodiments, the predictive model is trained using at least a portion of a de-identified training dataset. In various embodiments, the de-identified training dataset comprises one or more training MCFs comprising fields with patient data from de-identified electronic medical record (EMR) data.

In various embodiments, the de-identified training dataset is generated by: obtaining the de-identified electronic medical record (EMR) data comprising patient data and patient identifiers, wherein the patient identifiers enable distinguishing patient data of different patients, but does not enable identification of patients; and generating the one or more training MCFs using the patient data from the de-identified EMR data. In various embodiments, generating the one or more training MCFs using the patient data from the de-identified EMR data comprises: for at least one of the one or more training MCFs, assigning or having assigned one or more labels to a field of the training MCF. In various embodiments, the one or more labels assigned to a field comprises two or more, three or more, four or more, five or more, six or more, seven or more, eight or more, nine or more, ten or more, fifteen or more, twenty or more, twenty five or more, thirty or more, forty or more, fifty or more, or a hundred or more labels assigned to a field. In various embodiments, the patient data comprises one or more of a disease condition, suspect detail, disposition, annual care visit date, provider group identifier, line of business, contract identifier, and incentive program.

In various embodiments, the de-identified training dataset comprises between 20 and 1 million training MCFs. In various embodiments, the training MCFs comprise between 2 and 5000 unique labels assigned to fields of the training MCFs. In various embodiments, each unique label is assigned to a field in at least 10 training MCFs. In various embodiments, the training MCFs are in any of a text, PDF, TIFF, image format, or ZIP file. In various embodiments, the at least the portion of the de-identified training dataset is selected by: applying a filtering model to one or more training MCFs of the de-identified training dataset, wherein the filtering model classifies a training MCF as one of within or out of domain. In various embodiments, training MCFs that are classified by the filtering model as within domain are selected as the portion of the de-identified training dataset used to train the predictive model. In various embodiments, training MCFs that are classified by the filtering model as out of domain are withheld from being selected as the portion of the de-identified training dataset used to train the predictive model. In various embodiments, the patient identifier is a X digit unique pin, wherein X is at least 4, at least 5, at least 6, at least 7, at least 8, at least 9, or at least 10 digits in length.

In various embodiments, providing the populated MCF comprises providing the populated MCF to a healthcare professional. In various embodiments, methods disclosed herein further comprise: receiving feedback on the populated MCF, wherein the feedback comprises one or more of: an approval of the populated MCF, or a modification to patient data in one or more fields in the MCF. In various embodiments, providing the populated MCF further comprises providing supporting documentation. In various embodiments, the supporting documentation comprises portions of the patient data for supporting usage of one or more codes included in the populated MCF. In various embodiments, the one or more codes comprise ICD-10 codes, Current Procedural Terminology (CPT) codes, Healthcare Common Procedure Coding System (HCPCS) codes, G-codes, or hierarchical condition categories (HCC) codes. In various embodiments, the entity is a hospital or an online database. In various embodiments, the online database is one of Snomed CT, OpenEHR, or EPIC.

In various embodiments, the predictive model is trained to predict a single label. In various embodiments, the predictive model is trained to predict two or more labels. In various embodiments, each label is one of a disease label, an entity label, a sentiment label, a risk label, a code label, a score, a disease state, or an insurance specific policy. In various embodiments, the score is a RAF score or a HEDIS score. In various embodiments, the transmission of the patient identifier and receiving the corresponding patient data of the patient without receiving the identity of the patient ensures Healthcare Insurance Portability and Accountability Act (HIPAA) compliance. In various embodiments, the predictive model further analyzes the corresponding patient data or additional data derived from the corresponding patient data using a clinical taxonomy database to output the decisions. In various embodiments, the clinical taxonomy database comprises one or more codes. In various embodiments, the one or more codes comprise ICD-10 codes, Current Procedural Terminology (CPT) codes, Healthcare Common Procedure Coding System (HCPCS) codes, G-codes, or hierarchical condition categories (HCC) codes. In various embodiments, the clinical taxonomy database further comprises one or more documented diseases. In various embodiments, the clinical taxonomy database is structured to relationally connect a documented disease with a code. In various embodiments, the clinical taxonomy database further comprises a quality patient outcome score indicative of an improvement of patient care corresponding to the documented disease and the code.

Additionally disclosed herein is a non-transitory computer readable medium comprising instructions that, when executed by a processor, cause the processor to: obtain an unfilled medical compliance form (MCF); identify one or more fields for populating health data of a patient, the patient associated with a patient identifier; transmit the patient identifier to an entity, wherein the entity has access to the patient identifier, an identity of the patient, and corresponding patient data of the patient; receive, from the entity, the corresponding patient data of the patient without receiving the identity of the patient; deploy a predictive model to analyze the one or more fields, wherein the predictive model outputs decisions that identify subsets of the patient data to be included in the one or more fields; populate the one or more fields of the unfilled MCF with the identified subsets of the patient data to generate a populated MCF for the patient; and provide the populated MCF. In various embodiments, the predictive model is trained using at least a portion of a de-identified training dataset. In various embodiments, the de-identified training dataset comprises one or more training MCFs comprising fields with patient data from de-identified electronic medical record (EMR) data. In various embodiments, the de-identified training dataset is generated by: obtaining the de-identified electronic medical record (EMR) data comprising patient data and patient identifiers, wherein the patient identifiers enable distinguishing patient data of different patients, but does not enable identification of patients; and generating the one or more training MCFs using the patient data from the de-identified EMR data. In various embodiments, generating the one or more training MCFs using the patient data from the de-identified EMR data comprises: for at least one of the one or more training MCFs, assigning or having assigned one or more labels to a field of the training MCF. In various embodiments, the one or more labels assigned to a field comprises two or more, three or more, four or more, five or more, six or more, seven or more, eight or more, nine or more, ten or more, fifteen or more, twenty or more, twenty five or more, thirty or more, forty or more, fifty or more, or a hundred or more labels assigned to a field. In various embodiments, the patient data comprises one or more of a disease condition, suspect detail, disposition, annual care visit date, provider group identifier, line of business, contract identifier, and incentive program. In various embodiments, the de-identified training dataset comprises between 20 and 1 million training MCFs. In various embodiments, the training MCFs comprise between 2 and 5000 unique labels assigned to fields of the training MCFs. In various embodiments, each unique label is assigned to a field in at least 10 training MCFs. In various embodiments, the training MCFs are in any of a text, PDF, TIFF, image format, or ZIP file.

In various embodiments, the at least the portion of the de-identified training dataset is selected by: applying a filtering model to one or more training MCFs of the de-identified training dataset, wherein the filtering model classifies a training MCF as one of within or out of domain. In various embodiments, training MCFs that are classified by the filtering model as within domain are selected as the portion of the de-identified training dataset used to train the predictive model. In various embodiments, training MCFs that are classified by the filtering model as out of domain are withheld from being selected as the portion of the de-identified training dataset used to train the predictive model. In various embodiments, the patient identifier is a X digit unique pin, wherein X is at least 4, at least 5, at least 6, at least 7, at least 8, at least 9, or at least 10 digits in length. In various embodiments, the instructions that cause the processor to provide the populated MCF further comprises instructions that, when executed by the processor, cause the processor to provide the populated MCF to a healthcare professional. In various embodiments, the instructions that, when executed by the processor, cause the processor to: receive feedback on the populated MCF, wherein the feedback comprises one or more of: an approval of the populated MCF, or a modification to patient data in one or more fields in the MCF. In various embodiments, the instructions that cause the processor to provide the populated MCF further comprises instructions that, when executed by the processor, cause the processor to provide supporting documentation. In various embodiments, the supporting documentation comprises portions of the patient data for supporting usage of one or more codes included in the populated MCF. In various embodiments, the one or more codes comprise ICD-10 codes, Current Procedural Terminology (CPT) codes, Healthcare Common Procedure Coding System (HCPCS) codes, G-codes, or hierarchical condition categories (HCC) codes.

In various embodiments, the entity is a hospital or an online database. In various embodiments, the online database is one of Snomed CT, OpenEHR, or EPIC. In various embodiments, the predictive model is trained to predict a single label. In various embodiments, the predictive model is trained to predict two or more labels. In various embodiments, each label is one of a disease label, an entity label, a sentiment label, a risk label, a code label, a score, a disease state, or an insurance specific policy. In various embodiments, the score is a RAF score or a HEDIS score. In various embodiments, the transmission of the patient identifier and receiving the corresponding patient data of the patient without receiving the identity of the patient ensures Healthcare Insurance Portability and Accountability Act (HIPAA) compliance. In various embodiments, the predictive model further analyzes the corresponding patient data or additional data derived from the corresponding patient data using a clinical taxonomy database to output the decisions. In various embodiments, the clinical taxonomy database comprises one or more codes. In various embodiments, the one or more codes comprise ICD-10 codes, Current Procedural Terminology (CPT) codes, Healthcare Common Procedure Coding System (HCPCS) codes, G-codes, or hierarchical condition categories (HCC) codes. In various embodiments, the clinical taxonomy database further comprises one or more documented diseases. In various embodiments, the clinical taxonomy database is structured to relationally connect a documented disease with a code. In various embodiments, the clinical taxonomy database further comprises a quality patient outcome score indicative of an improvement of patient care corresponding to the documented disease and the code.

Further details of the nature and advantages of the present disclosure can be found in the following detailed description taken in conjunction with the accompanying figures. The present disclosure is capable of modification in various respects without departing from the spirit and scope of the present disclosure. Accordingly, the figures and description of these embodiments are not restrictive.

BRIEF DESCRIPTION OF THE FIGURES

A better understanding of the features and advantages of the present disclosure will be obtained by reference to the following detailed description that sets forth illustrative embodiments, in which the principles of the disclosure are utilized in combination with the accompanying drawings.

Wherever practicable, similar or like reference numbers may be used in the figures and may indicate similar or like functionality. For example, a letter after a reference numeral, such as "third party entity 110A," indicates that the text refers specifically to the element having that particular reference numeral. A reference numeral in the text without a following letter, such as "third party entity 110," refers to any or all of the elements in the figures bearing that reference numeral (e.g. "third party entity 110" in the text refers to reference numerals "third party entity 110A" and/or "third party entity 110B" in the figures).

DETAILED DESCRIPTION

Definitions

Figure 1A:
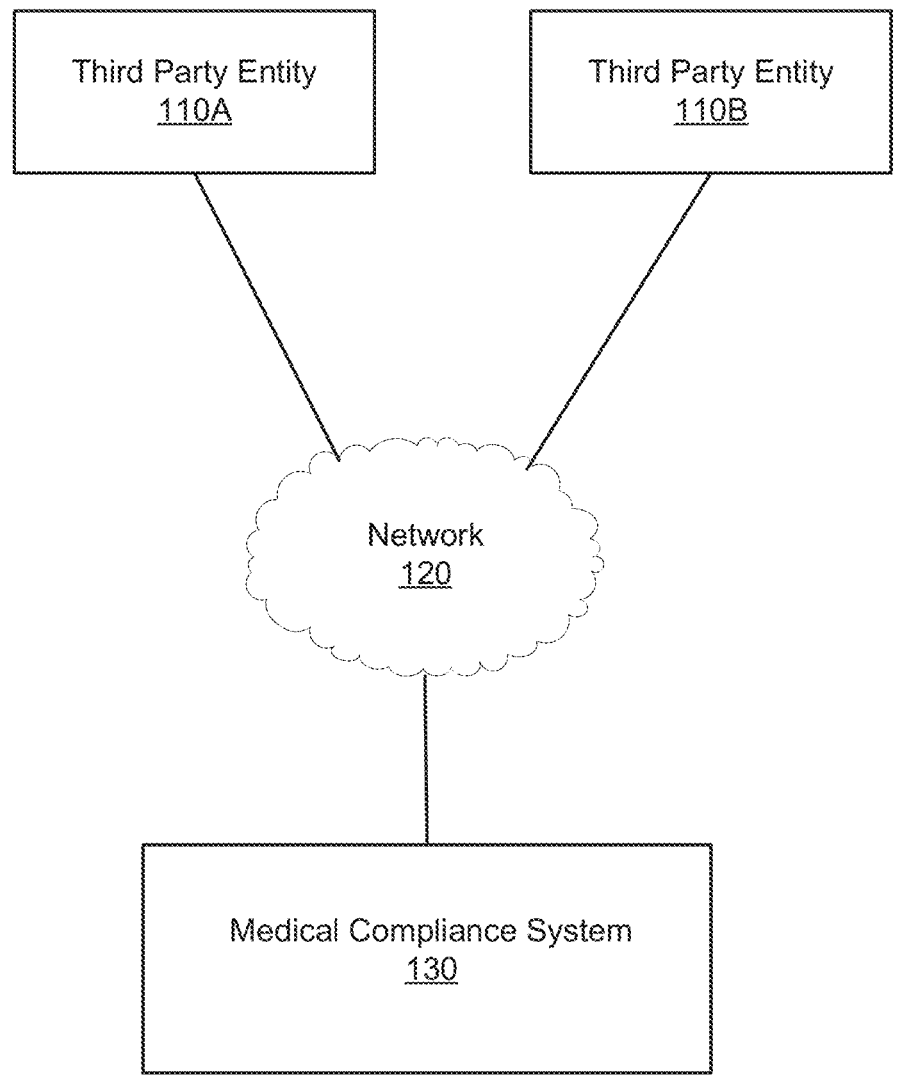
FIG. 1A is a schematic representation of an exemplary system overview that includes a medical compliance system and one or more third party entities, in accordance with an embodiment.

All technical and scientific terms used herein, unless otherwise defined below, are intended to have the same meaning as commonly understood by one of ordinary skill in the art. The mention of techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Throughout the description, where systems and compositions are described as having, including, or comprising specific components, or where processes and methods are described as having, including, or comprising specific steps, it is contemplated that, additionally, there are systems and compositions and kits of the present invention that consist essentially of, or consist of, the recited components, and that there are processes and methods according to the present invention that consist essentially of, or consist of, the recited processing steps.

In the disclosure, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a system or a method provided and described herein can be combined in a variety of ways without departing from the spirit and scope of the present disclosure and invention(s) herein, whether explicit or implicit herein. For example, where reference is made to a particular system, that system can be used in various embodiments of systems of the present disclosure and/or in methods of the present disclosure, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of invention(s) provided, described, and depicted herein.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

The articles "a" and "an" are used in this disclosure to refer to one or more than one (i.e., to at least one) of the grammatical object of the article, unless the context is inappropriate. By way of example, "an element" means one element or more than one element.

The term "and/or" is used in this disclosure to mean either "and" or "or" unless indicated otherwise.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

It should be understood that the order of steps or order for performing certain actions is immaterial so long as the present invention remain operable. Moreover, two or more steps or actions may be conducted simultaneously.

At various places in the present specification, variable or parameters are disclosed in groups or in ranges. It is specifically intended that the description include each and every individual subcombination of the members of such groups and ranges. For example, an integer in the range of 0 to 10 is specifically intended to individually disclose 0, 1, 2, 3, 4, 5, 6, 7, 8, 9, 10, and an integer in the range of 1 to 5 is specifically intended to individually disclose 1, 2, 3, 4, and 5.

The use of any and all examples, or exemplary language herein, for example, "such as" or "including," is intended merely to illustrate better the present disclosure and does not pose a limitation on the scope of any invention(s) unless claimed. No language in the specification should be construed as indicating any non-claimed element as essential to the practice of that provided by the present disclosure.

Terms used in the claims and specification are defined as set forth below unless otherwise specified.

The term "subject" or "patient" are used interchangeably and encompass a cell, tissue, organism, human or non-human, mammal or non-mammal, male or female, whether in vivo, ex vivo, or in vitro.

The phrases "medical compliance form" and "MCF" are used interchangeably and generally refer to medical forms that are to be filled out by healthcare providers for satisfying compliance requirements. Example medical compliance forms include patient assessment forms (PAFs), healthcare quality patient assessment forms (HQPAFs), nursing assessment forms, Attestation, policy document, and health insurance portability and accountability act (HIPAA) compliance forms. In various embodiments, medical compliance forms may be differently structured and have different formats. For example, different medical compliance forms from different sources can be structured with different data fields, different organizations, and different naming conventions.

The phrase "field" or "entry" in relation to a medical compliance form (MCF) refers to a portion of the MCF which can be populated with information, such as patient data. Example fields of a medical compliance form can be populated with any of the following: patient identifier, patient category, patient age, patient gender, patient contact information, patient name, patient date of birth, patient fitness, patient vital signs, patient past medical history, patient allergies, patient medications, patient symptoms, patient diagnosis, suspected hierarchical condition category (HCC) codes, suspected medical problems, suspected early screenings, suspected chronic care, and billing code. As disclosed herein, machine learning models are implemented to intelligently populate information into one or more fields of MCFs.

The phrase "machine learning implemented method" or "ML implemented method" refers to the implementation of a machine learning algorithm, such as, e.g., any of linear regression, logistic regression, decision tree, support vector machine classification, Naïve Bayes classification, K-nearest neighbor classification, random forest, deep learning, gradient boosting, generative adversarial networking learning, reinforcement learning, Bayesian optimization, matrix factorization, and dimensionality reduction techniques such as manifold learning, principal component analysis, factor analysis, autoencoder regularization, and independent component analysis, or a combination thereof.

II. Overview

Generally, disclosed herein are methods for intelligently populating medical compliance forms (MCFs) with at least patient data to meet compliance requirements (e.g., meeting patient data compliance requirements such as HIPAA requirements, as well as compliance requirements concerning patient forms). As discussed in further detailed below, methods involve training and deploying machine learning models that can appropriately analyze a wide array of MCFs with varying formats. For one or more fields of a MCF, the machine learning model analyzes the field and outputs a prediction as to patient data that is to be populated into field. Furthermore, the machine learning model is exposed only to de-identified patient data (e.g., to respect patient data compliance requirements). The analysis performed by the machine learning model is agnostic as to patient identity, and therefore, can be rapidly iterated across numerous medical compliance forms. Altogether, methods disclosed herein achieved adherence to compliance requirements, which will ultimately lead to improved patient outcomes. In an embodiment, aspects of the present disclosure can be used to improve medical reporting compliance in comparison to Risk Adjustment Data Validation (RADV) audits. For instance, aspects of the present disclosure may allow for automatic digital recordation of medical, patient, and/or other data.

FIG. 1A is a schematic representation of an exemplary system overview that includes a medical compliance system and one or more third party entities, in accordance with an embodiment. Specifically, FIG. 1A introduces a medical compliance system 130 connected to one or more third party entities 110 (e.g., third party entity 110A and/or third party entity 110B) via a network 120. Although FIG. 1A depicts a medical compliance system 130 connected to two separate third party entities 110A and 110B, in various embodiments, the medical compliance system 130 can be connected to additional third party entities (e.g., tens, or even hundreds, or more third party entities). In particular embodiments, the medical compliance system 130 can be connected to at least 5 third party entities. In particular embodiments, the medical compliance system 130 can be connected to at least 10 third party entities.

Referring first to the third party entity 110, the third party entity 110 can be a partner entity of the medical compliance system 130. In various embodiments, the third party entity 110 can provide information, such as patient data, to the medical compliance system 130. For example, the third party entity 110 may harbor a patient database including patient data for a plurality of patients (e.g., patient data for tens, hundreds, thousands, or millions of patients). In various embodiments, the third party entity is a hospital. For example, the hospital may harbor a patient database including patient data for patients of the hospital. In various embodiments, the patient database may be an online database (e.g., a cloud online database). In various embodiments, the third party entity is an online database (e.g., a cloud online database). For example, the third party entity may be an online database that is independently operated by a party that is separate from a hospital. Example online databases include Snomed CT, OpenEHR, or EPIC. In various embodiments, patient data includes any data relevant to a patient including Patient Condition, Suspect Detail, Disposition (e.g., if an account is open or closed), Annual Care Visit Date, Provider Group ID, Line of Business (e.g., insurance plan), Contract ID (e.g., short code of a health plan), and Incentive Program (e.g., in office assessment or care gaps representing incentives for completing MCFs).

In various embodiments, the medical compliance system 130 can interact with the third party entities 110 to access patient data while meeting patient data compliance requirements (e.g., HIPAA requirements). In particular embodiments, the medical compliance system 130 sends requests to and receive patient data from third party entities 110 without receiving access to patient identities. For example, the medical compliance system 130 can provide requests to third party entities 110, where requests include a patient identifier (e.g., an identification number). Here, the patient identifier is sufficient to identify the corresponding patient data, but does not, by itself, reveal the identity of the patient (e.g., name, gender, age or the patient). Thus, the third party entity, which has access to the patient identity, patient data, and patient identifier, can appropriately handle the request and return the requested patient data to the medical compliance system 130 without returning the patient identity. This ensures that the medical compliance system 130 only accesses de-identified patient data in accordance with patient data compliance requirements (e.g., HIPAA requirements). Thus, the medical compliance system 130 can deploy trained machine learning models to intelligently populate medical compliance forms with portions of the de-identified patient data.

In various embodiments, the medical compliance system 130 provides populated medical compliance forms to third party entities 110 to satisfy compliance requirements. For example, populated medical compliance forms may include information regarding patient data as well as suggested medical categorization (e.g., suggested procedures, diagnostics, therapies, billing codes, or patient scores) for a patient. Thus, the third party entity 110 can accurately track the medical categorization of the patients. In various embodiments, in response to receiving the populated medical compliance from the medical compliance system 130, third party entity 110 can further provide payment or compensation to the medical compliance system 130 in view of the medical categorization identified in the populated medical compliance forms.

Referring next to the network 120, the disclosure contemplates any suitable network 120 that enables connection between the medical compliance system 130 and third party entities 110A and 110B. For example, the medical compliance system 130 can provide a request to a third party entity 110 via the network 120 for patient data. The network 120 may comprise any combination of local area and/or wide area networks, using both wired and/or wireless communication systems. In one embodiment, the network 120 uses standard communications technologies and/or protocols. For example, the network 120 includes communication links using technologies such as Ethernet, 802.11, worldwide interoperability for microwave access (WiMAX), 3G, 4G, code division multiple access (CDMA), digital subscriber line (DSL), etc. Examples of networking protocols used for communicating via the network 120 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 120 may be represented using any suitable format, such as hypertext markup language (HTML) or extensible markup language (XML). In some embodiments, all or some of the communication links of the network 120 may be encrypted using any suitable technique or techniques.

III. Medical Compliance System

Figure 1B:
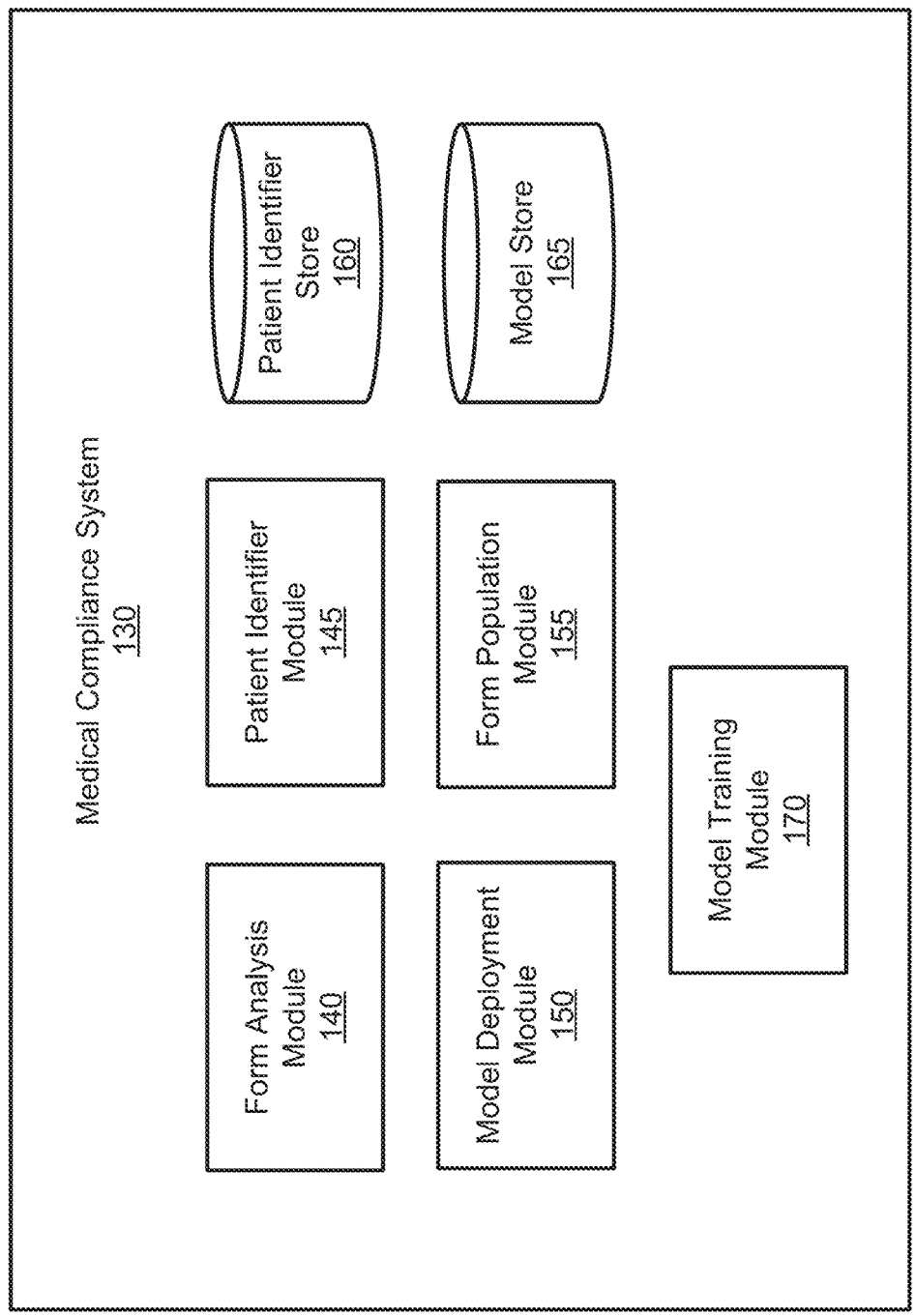
FIG. 1B is a block diagram of an exemplary medical compliance system, in accordance with an embodiment.

Generally, the medical compliance system trains and deploys machine learning models to intelligently populate medical compliance forms. By doing so, the medical compliance system can improve compliance amongst healthcare providers and furthermore, can provide suggested medical categorization (e.g., suggested procedures, diagnostics, therapies, billing codes, or patient scores) for patients to improve overall patient outcomes. FIG. 1B is a block diagram of an exemplary medical compliance system 130, in accordance with an embodiment. The exemplary medical compliance system 130 is introduced to show example modules including the form analysis module 140, the patient identifier module 145, the model deployment module 150, the form population module 155, and the model training module 170. In various embodiments, the medical compliance system 130 may further include a storage, such as a patient identifier store 160 (e.g., for storing patient identifiers) and/or a model store 160 (e.g., for storing one or more machine learning models).

Generally, the form analysis module 140 analyzes an unfilled medical compliance form (MCF) to determine presence of one or more fields within the MCF. In various embodiments, the form analysis module 140 analyzes contextual characteristics around fields of a MCF to determine the type of information that is to be included in the fields. Thus, given the contextual characteristics of the fields of the MCF, the form analysis module 140 can select the appropriately trained predictive model to be deployed for the MCF.

The patient identifier module 145 retrieves a patient identifier (e.g., from patient identifier store 160) and performs the steps for requesting and obtaining patient data from a third party entity (e.g., third party entity 110 shown in FIG. 1A). Generally, the steps performed by the patient identifier module 145 ensures that the medical compliance system 130 accesses the relevant patient data to be incorporated into the fields of a medical compliance form, while adhering to the patient data compliance requirements (e.g., HIPAA requirements). For example, the patient identifier module 145 transmits a request including a patient identifier to the third party entity for corresponding patient data. The patient identifier module 145 receives, from the third party entity, the corresponding patient data, but no data that can be used to identify the identity of the patient. Thus, the patient identifier module 145 can obtain de-identified patient data in accordance with patient data compliance requirements.

The model deployment module 150 retrieves the appropriately trained predictive model (e.g., from model store 165) and deploys the predictive model for purposes of preparing a medical compliance form. In various embodiments, the model deployment module 150 provides, as input to a trained predictive model, the one or more fields identified by the form analysis module 140 and patient data obtained by the patient identifier module 145. The predictive model outputs decisions as to which portions of the patient data are best suited for inclusion in which fields of the medical compliance form.

The form population module 155 populates the fields of a medical compliance form in accordance with the decisions outputted by the trained predictive model. For example, the form population module 155 may incorporate medication that a patient is currently taking, as indicated by the trained predictive model, into a field in the medical compliance form that inquires for prior medication history of the patient. As another example, the form population module 155 may incorporate one or more billing codes, as indicated by the trained predictive model, into a field identifying suggested medical categorizations (e.g., suggested procedures, diagnostics, therapies, billing codes, or patient scores) for the patient. Thus, the form population module 155 generates a fully populated medical compliance form. In various embodiments, the form population module 155 can provide the populated medical compliance form e.g., to a healthcare provider for review or e.g., to a third party for confirmation and/or payment.

IV. Exemplary Methods (a) Identification of Fields of a Medical Compliance Form (MCF)

The medical compliance system 130 (e.g., and more specifically the form analysis module 140) may obtain an unfilled medical compliance form (MCF) that is to be populated with at least patient data for a particular patient. In various embodiments, the MCF may have a particular format, such that the fields in the MCF that are to be populated may be unique to that particular format. In various embodiments, the MCF may have a particular format that is dependent on a third party (e.g., third party entity 110). For example, the MCF may have originated from a third party insurer, examples of which include Optum, United Healthcare, Wellmed, and Devoted, and therefore, the MCF may include one or more fields that are specific or unique to the third party insurer.

Generally, the form analysis module 140 analyzes the unfilled MCF and/or one or more fields of the MCF. In various embodiments, the form analysis module 140 performs an analysis of the MCF and/or fields of the MCF by performing a document scan of the MCF to identify contextual characteristics of fields of the MCF. Contextual characteristics refer to clinical context of a field, such as a location of the field within the MCF, position of the field relative to other fields in the MCF, and/or text associated with a field (e.g., a header of the field or a text describing the field).

In various embodiments, the form analysis module 140 analyzes the unfilled MCF and/or one or more fields of the MCF to identify a particular format of the MCF.

As one example, the form analysis module 140 analyzes the unfilled MCF to determine whether the MCF is one of a patient assessment form (PAFs), healthcare quality patient assessment form (HQPAFs), nursing assessment form, attestation, policy document, or health insurance portability and accountability act (HIPAA) compliance form. As another example, based on the contextual characteristics of fields of the MCF (e.g., location/position of fields, text associated with fields), the form analysis module 140 can identify the particular format of the MCF. In various embodiments, based on the contextual characteristics of fields of the MCF, the form analysis module 140 can identify a particular format of the MCF that is used or preferred by a third party (e.g., third party insurer, examples of which include Optum, United Healthcare, Wellmed, and Devoted). In various embodiments, the form analysis module 140 may identify an appropriate predictive model that was trained to analyze MCFs of that particular format. In such embodiments, predictive models are trained to analyze MCFs with specific formats. Therefore, a predictive model trained to analyze MCFs of a first format may not perform as expected for MCFs of a different, second format.

(b) Requesting and Obtaining Patient Data

Figure 2A:
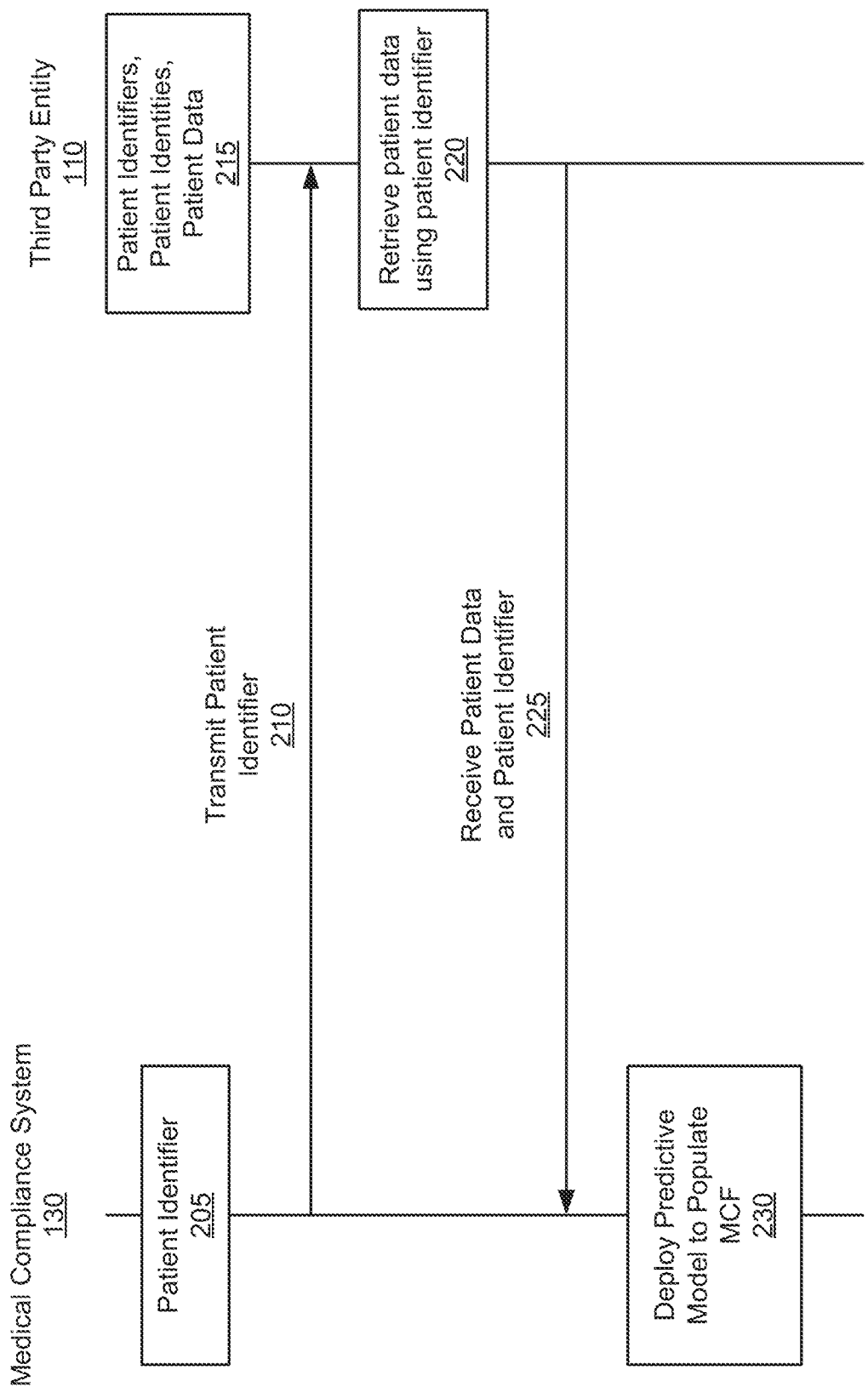
FIG. 2A is an example interaction diagram between the medical compliance system and one or more third party entities for generating populated medical compliance forms, in accordance with an embodiment.

FIG. 2A is an example interaction diagram between the medical compliance system and one or more third party entities for generating populated medical compliance forms, in accordance with an embodiment. Generally, the process shown in FIG. 2A ensures that the medical compliance system 130 can access patient data in accordance with patient data compliance requirements (e.g., HIPAA requirements).

As shown in FIG. 2A, the medical compliance system 130 stores patient identifiers (e.g., patient identifier 205) and the third party entity 110 stores patient identifiers, patient identities, and patient data 215. Although not shown in FIG. 2A, the medical compliance system 130 and the third party entity 110 may have previously collaborated to exchange patient identifiers. Therefore, both the medical compliance system 130 and the third party entity 110 have matching patient identifiers. In various embodiments, a patient identifier is a X-digit code. Such a X-digit code may be randomly assigned to a patient. In various embodiments, the patient identifier is a 3 digit, 4 digit, 5 digit, 6 digit, 7 digit, 8 digit, 9 digit, 10 digit, 11 digit, 12 digit, 13 digit, 14 digit, 15 digit, 16 digit, 17 digit, 18 digit, 19 digit, or 20 digit code. In particular embodiments, the patient identifier is a 10 digit code.

The third party entity 110 may structure the patient identifiers, patient identities, and patient data such that it can readily provide data to the medical compliance system 130 in accordance with patient data compliance requirements (e.g., HIPAA requirements). For example, the third party entity 110 may store a first dataset that includes patient identifiers and corresponding patient identities. The third party entity 110 may additionally store a second dataset that includes patient identifiers and corresponding patient data.

Here, the second dataset does not include patient identities. Thus, the third party entity 110 can provide the second dataset (e.g., patient identifiers and patient data, but not patient identities) in accordance with patient data compliance requirement while keeping the first dataset on premises. Thus, patient identities included in the first dataset are not transmitted outside of the third party entity 110.

As shown in FIG. 2A, at step 210, the medical compliance system 130 (e.g., more specifically, the patient identifier module 145) transmits a patient identifier to the third party entity 110. Here, the medical compliance system 130 transmits the patient identifier in the form of a request for patient data corresponding to the patient identifier. In various embodiments, the medical compliance system 130 transmits a request including the patient identifier after analyzing one or more fields of an unfilled medical compliance form. Thus, the medical compliance system 130 transmits the request to obtain corresponding patient data that can be used to populate the one or more fields of the unfilled medical compliance form.

The third party entity 110 retrieves (e.g., step 220) the patient data corresponding to the patient identifier and transmits the patient data to the medical compliance system 130. Specifically, as shown in FIG. 2A, at step 225, the medical compliance system 130 receives the corresponding patient data from the third party entity 110. In various embodiments, at step 225, the medical compliance system 130 further receives the patient identifier. Thus, given the patient identifier, the medical compliance system 130 can associate the received patient data with the appropriate request (e.g., the prior request sent at step 210).

As shown at step 230, the medical compliance system 130 deploys a trained predictive model to populate a medical compliance form using the received patient data. Specifically, the trained predictive model outputs decisions as to which portions of the patient data are best suited for inclusion in which fields of the medical compliance form. Further details of the deployment of the predictive model for populating a medical compliance form are described herein.

(c) Intelligently Populating a Medical Compliance Form with Patient Data

Figure 2B:
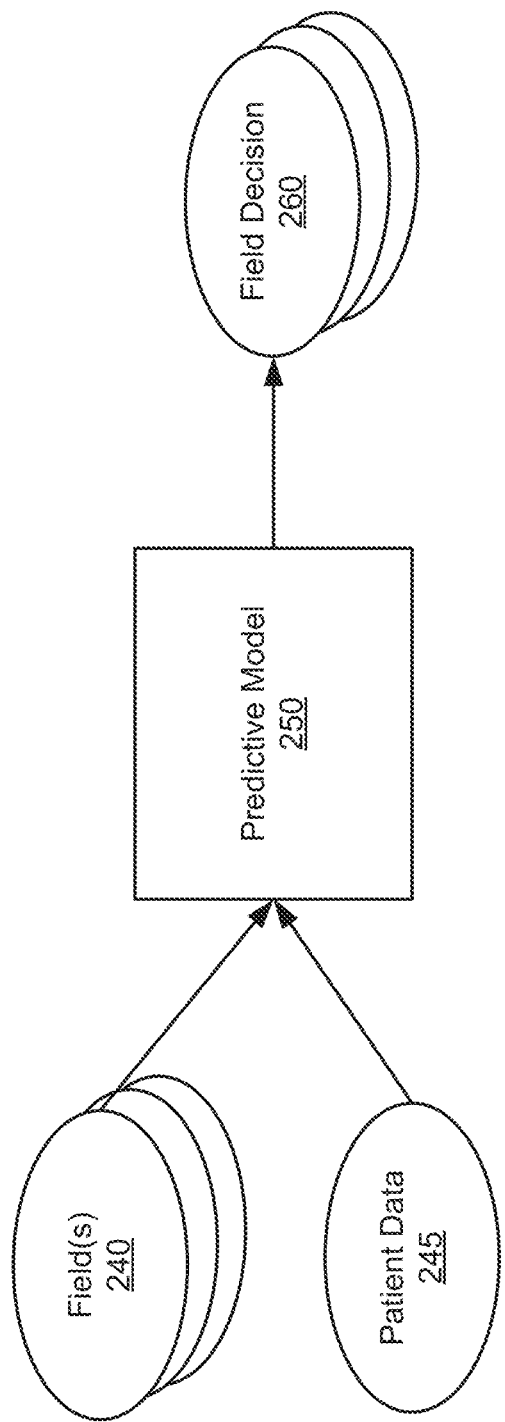
FIG. 2B is an example flow diagram showing the operation of a predictive model, in accordance with an embodiment.

FIG. 2B is an example flow diagram showing the operation of a predictive model, in accordance with an embodiment. In the embodiment shown in FIG. 2B, the predictive model 250 receives, as input, one or more fields 240 of a single medical compliance form as well as patient data 245 for a patient e.g., obtained from a third party entity. The predictive model outputs field decisions 260. A field decision 260 refers to a prediction of a portion of the patient data 245 that is suggested to be inputted into a field 240. Thus, in various embodiments, the number of field decisions 260 outputted by the predictive model 250 aligns with the number of fields 240 inputted to the predictive model 250.

In various embodiments, the number of fields 240 analyzed by the predictive model 250 includes at least 10, at least 20, at least 30, at least 40, at least 50, at least 60, at least 70, at least at least 90, at least 100, at least 150, at least 200, at least 250, at least 300, at least 400, at least 500, at least 600, at least 700, at least 800, at least 900, or at least 1000 fields of a medical compliance form.

In various embodiments, the fields 240 analyzed by the predictive model 250 include contextual characteristics of the fields, including position of the fields in the MCF and/or text describing the fields. Thus, the predictive model 250 can analyze the contextual characteristics of the fields 240 in determining which portions of the patient data 245 are to be included in the fields.

In various embodiments, the predictive model 250 comprises a natural language processing model that analyzes the contextual characteristics of the fields as well as the text of the patient data 245 and determines which portions of the patient data are best suited for inclusion in the fields. For example, the natural language processing model may recognize text of the patient data and understand that such text is relevant for the contextual characteristics of a field. In various embodiments, the predictive model is any one of a regression model (e.g., linear regression, logistic regression, or polynomial regression), decision tree, random forest, support vector machine, Naïve Bayes model, k-means cluster, or neural network (e.g., feed-forward networks, convolutional neural networks (CNN), deep neural networks (DNN)). In various embodiments, the predictive model is trained using a machine learning implemented method, such as any one of a linear regression algorithm, logistic regression algorithm, decision tree algorithm, support vector machine classification, Naïve Bayes classification, K-Nearest Neighbor classification, random forest algorithm, deep learning algorithm, gradient boosting algorithm, dimensionality reduction techniques, or combinations thereof.

Although FIG. 2B shows the deployment of the predictive model for fields of a single medical compliance form, in various embodiments, the predictive model can be iteratively deployed to analyze fields for additional medical compliance forms. In various embodiments, multiple instances of the predictive model 250 are deployed sequentially to analyze fields of medical compliance forms. In various embodiments, multiple instances of the predictive model 250 are deployed in parallel to analyze fields of medical compliance forms.

In various embodiments, the predictive model employs a clinical taxonomy database, such as a relational database, to analyze the contextual characteristics of fields and to output the field decision(s) 260. As described herein, a clinical taxonomy database may represent a relational database that stores one or more of codes (e.g., ICD-10 codes, Current Procedural Terminology (CPT) codes, Healthcare Common Procedure Coding System (HCPCS) codes, G-codes, or hierarchical condition categories (HCC) codes), documented diseases, a score (e.g., a risk adjustment factor (RAF) score or a quality patient outcome score, such as a HEDIS score). In various embodiments, the clinical taxonomy database is structured to relationally connect a documented disease with a code. In various embodiments, the clinical taxonomy database is structured to relationally connect a documented disease with a code and further to a score (e.g., a RAF or HEDIS score).

In various embodiments, the predictive model uses the data stored in the clinical taxonomy database to guide the output decisions. In various embodiments, the predictive model can output one or more decisions that indicate the relationally connected information in the clinical taxonomy database. For example, the predictive model can output one or more decisions that indicate that one or more fields of the MCF are to include a documented disease, a code, and a score, where the documented disease, the code, and the score are each relationally connected in the clinical taxonomy database. In various embodiments, the relationally connected information in the clinical taxonomy database represents potential options that the predictive model can analyze such that the predictive model can select one of the options for inclusion as the output decision. Thus, the combination of the predictive model and the clinical taxonomy database generates output decisions for populating a MCF, such that the populated MCF includes improved and more comprehensive information that a healthcare provider may not have considered including.

Figure 2C:
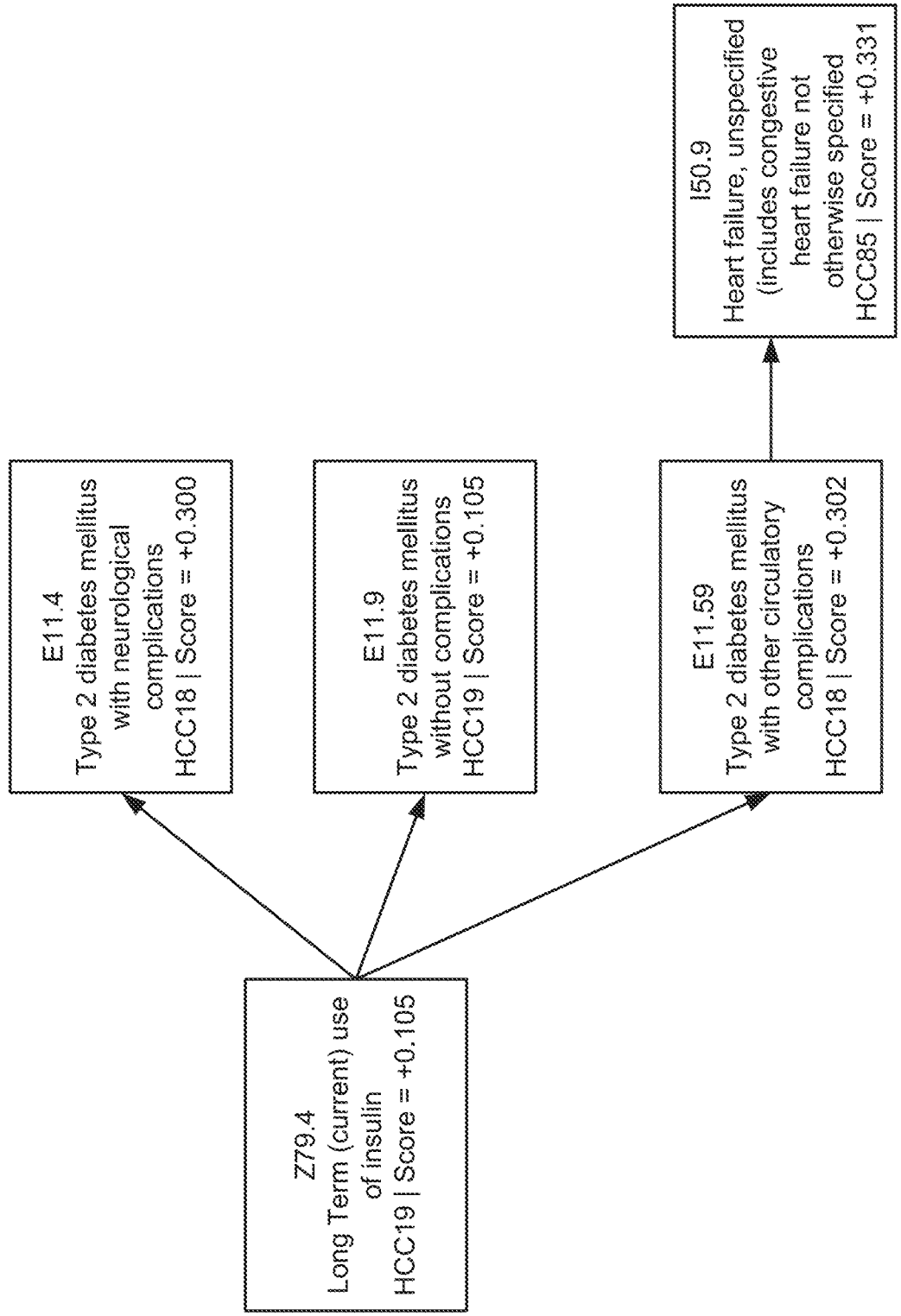
FIG. 2C is an example depiction of decision-making of a predictive model in combination with a clinical taxonomy database, in accordance with an embodiment.

To provide an example, reference is now made to FIG. 2C which is an example depiction of decision-making of a predictive model in combination with a clinical taxonomy database, in accordance with an embodiment. As shown in FIG. 2C, there may be different options for which the predictive model can use to output a decision. The options may be guided by relationally structured data in a clinical taxonomy database. For example, beginning at the left in FIG. 2C, the clinical taxonomy database may structurally relate the ICD-10 code "Z79.4" with a diagnosis of "Long term (current) use of insulin" and further with a score of "0.105." Here, the score may represent e.g., a HEDIS score. Based on this first set of relational information (e.g., Z79.4, Long term (current use of insulin, and score=+0.105), the clinical taxonomy database may further include additional sets of relational information. For example, a first additional set of relational information can identify a more specific diagnosis of "Type 2 diabetes mellitus with neurological complications." This in turn is stored in the clinical taxonomy database and structurally related to the ICD-10 code of "E11.4" and Score=+0.302. A second additional set of relational information can identify the specific diagnosis of "Type 2 diabetes mellitus without complications" and is structurally related to the ICD-10 code of "E11.9" and Score=+0.105. The third additional set of relational information can identify the specific diagnosis of "Type 2 diabetes mellitus with other circulatory complications" and is structurally related to the ICD-10 code of "E11.59" and Score=+0.302. As further shown in FIG. 2C, there may be yet an additional set of relational information that identifies a specific diagnosis of "Heart failure, unspecified (includes congestive heart failure not otherwise specified)" which is structurally related to the ICD-10 code of "I50.9" and a Score=+0.331. Thus, in the example shown in FIG. 2C, the clinical taxonomy database provides the guided options based on the relationally stored information in the database. Although FIG. 2C shows a simplified diagram in which there is one option at a first level (e.g., far left with ICD code Z79.4), three options at a second level (e.g., middle of FIG. 2C with ICD codes E11.4, E11.9, and E11.59), and one option at a third level (e.g., right side of FIG. 2C with ICD code I50.9), in other embodiments, there may be more complex paths with more options at each level and/or more levels.

The predictive model can generate the output decision for a patient according to the guided options shown in FIG. 2C. For example, for a patient with a past history of long term use of insulin, the predictive model can choose a path to generate the output decision. As an example, the predictive model can choose a path that maximizes the score (e.g., HEDIS score) at each step. For example, the predictive model can begin at the left with ICD-10 code "Z79.4," and then proceed with the bottom option (ICD-10 code E11.59) given a score of +0.302. The predictive model can further proceed with bottom right option (ICD-10 code I50.9) given a score of +0.331. Thus, the output decision from the predictive model can include at least the ICD-10 code=I50.9, the diagnosis of Heart failure, and/or the score=+0.331. The output decision can then be subsequently used to populate the appropriate fields of a MCF, as is described in further detail herein.

In various embodiments, the field decision(s) 260 outputted by the predictive model may include suggested medical categorization (suggested procedures, diagnostics, therapies, billing codes, or patient scores) for inclusion in a field 240, where the suggested categorization may improve the outcome of a patient. In particular embodiments, the suggested medical categorization includes at least a code such as any of a ICD-10 code, Current Procedural Terminology (CPT) code, Healthcare Common Procedure Coding System (HCPCS) code, G-code, or hierarchical condition categories (HCC) code. In various embodiments, the code is associated with a suggested procedure, diagnosis, or therapy that can lead to improved outcome for the patient. Thus, healthcare providers may provide medical care in the form of the suggested procedure, diagnosis, or therapy to the patient.

In various embodiments, the code is associated with a score, such as a risk adjustment factor (RAF) score that is useful for predicting costs for the patient corresponding to the code. For example, the RAF score reflects the risk calculated by the patient's problem list and chronic disease status. The RAF score may reflect the predicted cost of the patient (e.g., reimbursement in the following performance year as a capitated payment) if the code is inputted for the patient. In various embodiments, the code is associated with a score, such as a Healthcare Effectiveness Data and Information Set (HEDIS) score. Here, the HEDIS score reflects the improved patient outcome of the patient corresponding to the code. For example, the HEDIS score is a performance improvement tool where various patient metrics are used to score a providers level of quality care performance. To provide an example scenario, a patient may show up presenting with diabetes and obesity. The healthcare provider may document the presence of diabetes and the weight of the patient, but may fail to include a diagnosis of obesity. In such a situation, the patient electronic medical records is likely incomplete as the weight of the patient is insufficient to establish patient obesity. If the incomplete electronic medical records are to be incorporated into a medical compliance form, the diagnosis of obesity may be further omitted. Here, by deploying the trained predictive model, the output of the predictive model can include a suggested medical categorization that identifies the patient as obese and therefore, suggests the inclusion of this characterization in a field of the medical compliance form. The suggested medical categorization may further include a score (e.g., a HEDIS score) that reflects the improved patient outcome if the patient is identified as obese.

Given the outputted field decisions 260, the form population module 155 (shown in FIG. 1B) populates the fields of the medical compliance form in accordance with the outputted field decisions 260. For example, the form population module 155 may incorporate medication that a patient is currently taking, as indicated by the trained predictive model, into a field in the medical compliance form that inquires for prior medication history of the patient. As another example, the form population module 155 may incorporate one or more codes, as indicated by the trained predictive model, into a field identifying suggested medical categorizations (e.g., suggested procedures, diagnostics, therapies, billing codes, or patient scores) for the patient.

(d) Training a Predictive Model

Embodiments disclosed herein involve training a predictive model such that the predictive model can be deployed to populate medical compliance forms. In various embodiments, the methods described in this section are performed by the model training module 170 (described in FIG. 1B). In various embodiments, the model training module 170 be deployed in a system separate from the medical compliance system 130. For example, the training of predictive models may be performed by a party that is different from a party that is operating the medical compliance system 130. In such embodiments, the training of predictive models and the deployment of predictive models are performed by separate parties. A first party who trains predictive models can then provide the trained predictive models to a second party for deploying the predictive models.

In various embodiments, the model training module 170 trains a predictive model using a training dataset comprising training medical compliance records (MCFs). A training MCF can be any of a text, PDF, TIFF, image format, or ZIP file. Here, the training MCFs include fields that have been populated with data, such as de-identified patient data (e.g., thereby complying with patient data compliance requirements (e.g., HIPAA requirements)). Hence, the training dataset can otherwise be referred to as a de-identified training dataset.

In various embodiments, the model training module 170 generates the training dataset by obtaining de-identified electronic medical record (EMR) data comprising patient data and patient identifiers and generating training MCFs including portions of the patient data from the de-identified EMR data. In various embodiments, the training MCFs include fields for which one or more labels have been assigned to the fields. Put another way, the model training module 170 trains a predictive model by: 1) obtaining the de-identified electronic medical record (EMR) data comprising patient data and patient identifiers, wherein the patient identifiers enable distinguishing patient data of different patients, but does not enable identification of patients; and 2) generating the one or more training MCFs using the patient data from the de-identified EMR data. The training MCFs represent the training dataset that can then be used to train predictive models.

In various embodiments, the training MCFs represent a diverse set of forms. For example, diverse forms can have different lengths, different formats, and different wording/styles. In various embodiments, diverse forms can originate from different third parties (e.g., different third party insurers, examples of which include Optum, United Healthcare, Wellmed, and Devoted) and therefore, the diverse forms can have different formats required by the different third parties. By including a diverse set of forms in the training dataset, the predictive model can be trained to better handle the diverse formats of the forms.

In various embodiments, to prepare the training MCFs for training a predictive model, methods involve assigning, to a field of a training MCF, one or more labels. A label, also referred to herein as an annotation, can be a name between two and thirty characters. Example labels can be a specific disease, a disease class, a link to lab values associated with another label, time values to associate chronology of symptoms and/or events, a modifier, or a composite mention. In various embodiments, preparing a training MCF for training a predictive model involves assigning, to a field of a training MCF, two or more, three or more, four or more, five or more, six or more, seven or more, eight or more, nine or more, ten or more, fifteen or more, twenty or more, twenty five or more, thirty or more, forty or more, fifty or more, or a hundred or more labels. In various embodiments, methods involve assigning between 2 and 5000 unique labels across the fields of the training MCFs of the training dataset. In various embodiments, methods involve assigning at least 5, at least 10, at least 20, at least 30, at least 40, at least 50, at least 100, at least 200, at least 300, at least 400, at least 500, at least 600, at least 700, at least 800, at least 900, at least 1000, at least 2000, at least 3000, at least 4000, or at least 5000 unique labels across the fields of the training MCFs of the training dataset.

In various embodiments, at least one of the labels is assigned to a field in at least 10 training MCFs. This ensures that the label shows up in the training MCFs with sufficient frequency for training of the predictive model. In various embodiments, at least 100, at least 200, at least 300, at least 400, at least 500, at least 600, at least 700, at least 800, at least 900, at least 1000, at least 2000, at least 3000, at least 4000, or at least 5000 labels are assigned to a field in at least 10 training MCFs. In various embodiments every label is assigned to a field in at least 10 training MCFs. In various embodiments, at least 100, at least 200, at least 300, at least 400, at least 500, at least 600, at least 700, at least 800, at least 900, at least 1000, at least 2000, at least 3000, at least 4000, or at least 5000 labels are assigned to a field in at least 50, at least 100, at least 150, or at least 200 training MCFs.

In various embodiments, the de-identified training dataset comprises between 20 and 1 million training MCFs. In various embodiments, the de-identified training dataset comprises at least 10, at least 20, at least 30, at least 40, at least 50, at least 100, at least 200, at least 300, at least 400, at least 500, at least 1000, at least 5000, at least 10,000, at least 50,000, at least 100,000, at least 50,000, or at least 10 million training MCFs.

In various embodiments, the most common label across the training MCFs is assigned to, at most, 100 times more training MCFs in comparison to the least common label. In various embodiments, the most common label across the training MCFs is assigned to, at most 90 times, at most 80 times, at most 70 times, at most 60 times, at most 50 times, at most 40 times, at most 30 times, at most 20 times, or at most 10 times more training MCFs in comparison to the least common label.

In various embodiments, the predictive model is trained using the training dataset. As described above, the training dataset includes training MCFs, which include populated fields (e.g., populated with patient data). The populated fields are additionally assigned one or more labels, which can serve as reference ground truths. In various embodiments, the data in the populated fields is provided as input to the predictive model. In various embodiments, the data in the populated fields are analyzed to extract contextual characteristics (e.g., a location of the field within the training MCF, position of the field relative to other fields in the training MCF, and/or text associated with a field (e.g., a header of the field or a text describing the field), which can then be provided as input to the predictive model. The predictive model can generate one or more predictions (e.g., a single label classification or a multi-label classification). Here, one or more predictions can be compared to the assigned labels and the model parameters of the predictive model are trained (e.g., adjusted) to improve the predictive power of the predictive model. In such embodiments, the predictive model is trained using supervised learning algorithms. In various embodiments, the predictive model is trained using unsupervised learning algorithms. In various embodiments, the predictive model has one or more parameters, such as hyperparameters or model parameters. Hyperparameters are generally established prior to training. Examples of hyperparameters include the learning rate, depth or leaves of a decision tree, number of hidden layers in a deep neural network, number of clusters in a k-means cluster, penalty in a regression model, and a regularization parameter associated with a cost function. Model parameters are generally adjusted during training. Examples of model parameters include weights associated with nodes in layers of neural network, support vectors in a support vector machine, and coefficients in a regression model.

In various embodiments, a filtering step can be applied to the training medical compliance forms (MCFs) prior to their use in training the predictive model. In some embodiments, the filtering step can be applied to remove training MCFs that would not be applicable for training a predictive model. In various embodiments, the filtering step involves applying a filtering model (also referred to herein as a document filtering model) which predicts whether a form fits within the current set of labels. As one example, the filtering step can remove training MCFs that originate from a different third party who has not previously provided medical compliance forms. As another example, the filtering step can remove training MCFs that include fields that do not fall within the current set of labels, also referred to as "out of domain" labels. For example, out of domain labels may be labels that show up too infrequently across the training dataset. Removing training MCFs with out of domain labels ensures that the predictive model is trained only using applicable training MCFs. Thus, these training MCFs with out of domain labels are withheld from the de-identified training dataset used to train the predictive model.

V. Exemplary Flow Process

Figure 3:
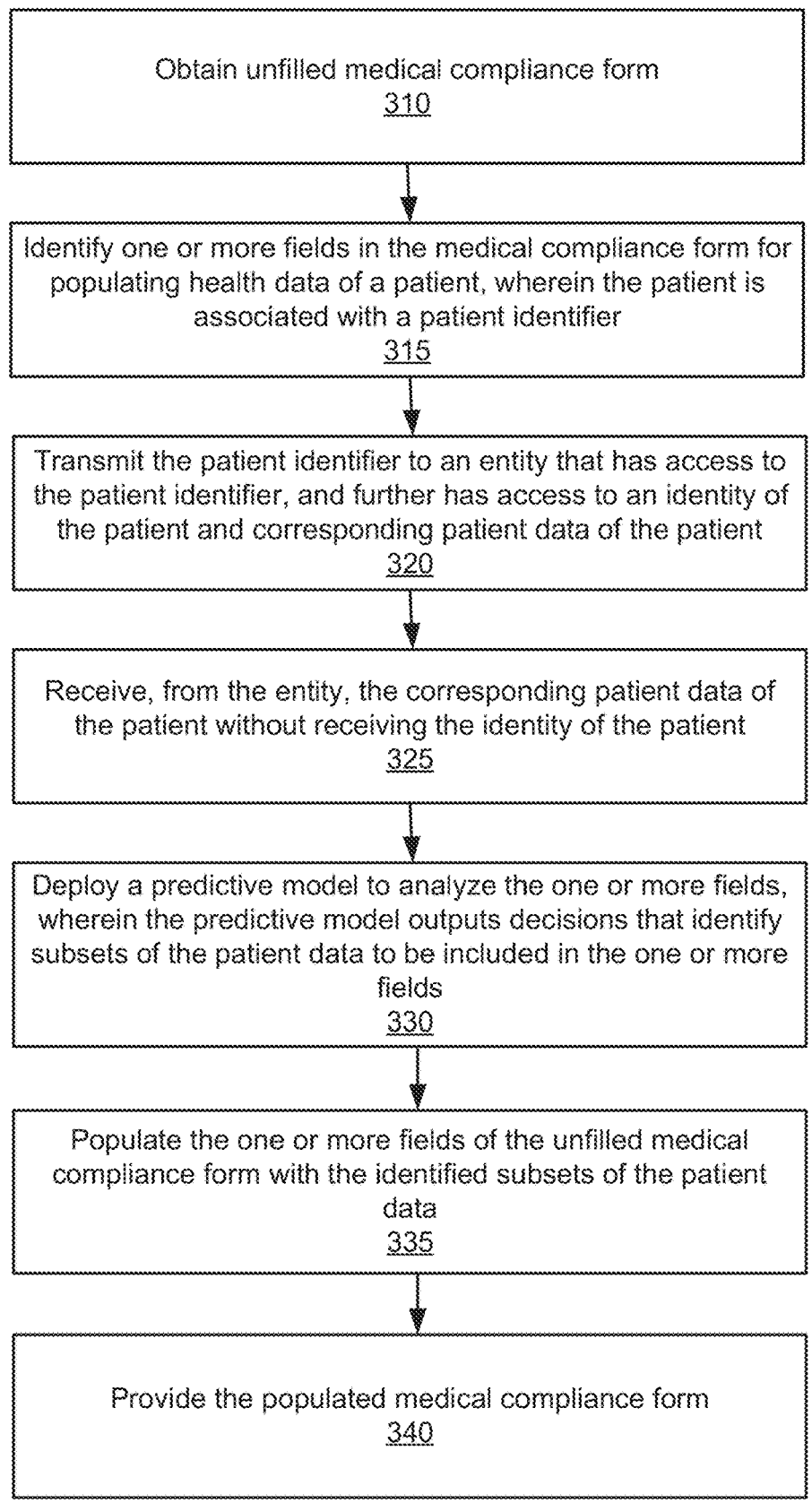
FIG. 3 is an example flow chart of an exemplary process for generating populated medical compliance forms, in accordance with an embodiment.

FIG. 3 is an example flow chart of an exemplary process for generating populated medical compliance forms, in accordance with an embodiment. In particular, FIG. 3 shows a process for populating a single medical compliance form. In various embodiments, the process shown in FIG. 3 can be performed multiple times to populate multiple medical compliance forms. In various embodiments, the process shown in FIG. 3 can be performed in parallel (e.g., in a batch fashion) to rapidly populate multiple medical compliance forms in a minimal amount of time.

Step 310 includes obtaining 310 an unfilled (e.g., blank) medical compliance form. In various embodiments, the medical compliance form may have a particular format (e.g., out of a plurality of possible formats) and includes one or more fields available for population.

Step 315 includes identifying one or more fields of the medical compliance form for populating health data of a patient. The patient is associated with a patient identifier. As described herein, the patient identifier is sufficient for identifying corresponding patient data, but is not sufficient for identifying the identity of the patient (e.g., patient name, gender, age).

Step 320 involves transmitting the patient identifier to an entity (e.g., third party entity) that has access to the patient identifier, identity of the patient, and corresponding patient data of the patient. The third party entity may be a hospital or an online database (e.g., Snomed CT, OpenEHR, or EPIC).

Step 325 involves receiving, from the third party entity, the corresponding patient data. Generally, the third party entity does not provide the identity of the patient. This ensures that patient data compliance requirements are met. Thus, de-identified patient data can be analyzed without any regard to the specific patient that the data was obtained from.

Step 330 involves deploying a trained predictive model to analyze one or more fields of the medical compliance form and the de-identified patient data. By doing so, the trained predictive model outputs one or more decisions that identify subsets of the patient data that are to be included in the one or more fields. For example, the trained predictive model accurately predicts that portions of the patient data relate to the patient's medical history (e.g., prior medications, prior indications, prior treatments/surgical interventions) and therefore, can output a decision that the portion of the patient data related to the patient's medical history should populate one or more patient medical history fields. As another example, the trained predictive model can output a decision that certain medical care that are likely to improve the patient outcome. Thus, the such medical care be included in one or more fields of the medical compliance form. In various embodiments, a healthcare provider can provide the suggested medical care to improve the patient outcome.

Step 335 involves populating the one or more fields of the medical compliance form with at least the identified subsets of the patient data included in the outputted decisions from the predictive model. Thus, step 335 generates a populated medical compliance form.

Step 340 involves providing the populated medical compliance form. In various embodiments, step 340 involves providing the populated medical compliance form to a healthcare provider, such that the healthcare provider can review the data included in the fields. In various embodiments, step 340 involves providing the populated medical compliance form to a third party entity to meet compliance requirements.

VI. Computer Embodiments

Also provided herein is a computer readable medium comprising computer executable instructions configured to implement any of the methods described herein. In various embodiments, the computer readable medium is a non-transitory computer readable medium. In some embodiments, the computer readable medium is a part of a computer system (e.g., a memory of a computer system). The computer readable medium can comprise computer executable instructions for performing methods disclosed herein, such as methods for performing the interface analysis and/or methods for discovering new therapeutic candidate molecules. The methods described above, including the methods for performing the interface analysis and/or methods for discovering new therapeutic candidate molecules are, in some embodiments, performed on a computing device. Examples of a computing device can include a personal computer, desktop computer laptop, server computer, a computing node within a cluster, message processors, hand-held devices, multi-processor systems, microprocessor-based or programmable consumer electronics, network PCs, minicomputers, mainframe computers, mobile telephones, PDAs, tablets, pagers, routers, switches, and the like.

Figure 4:
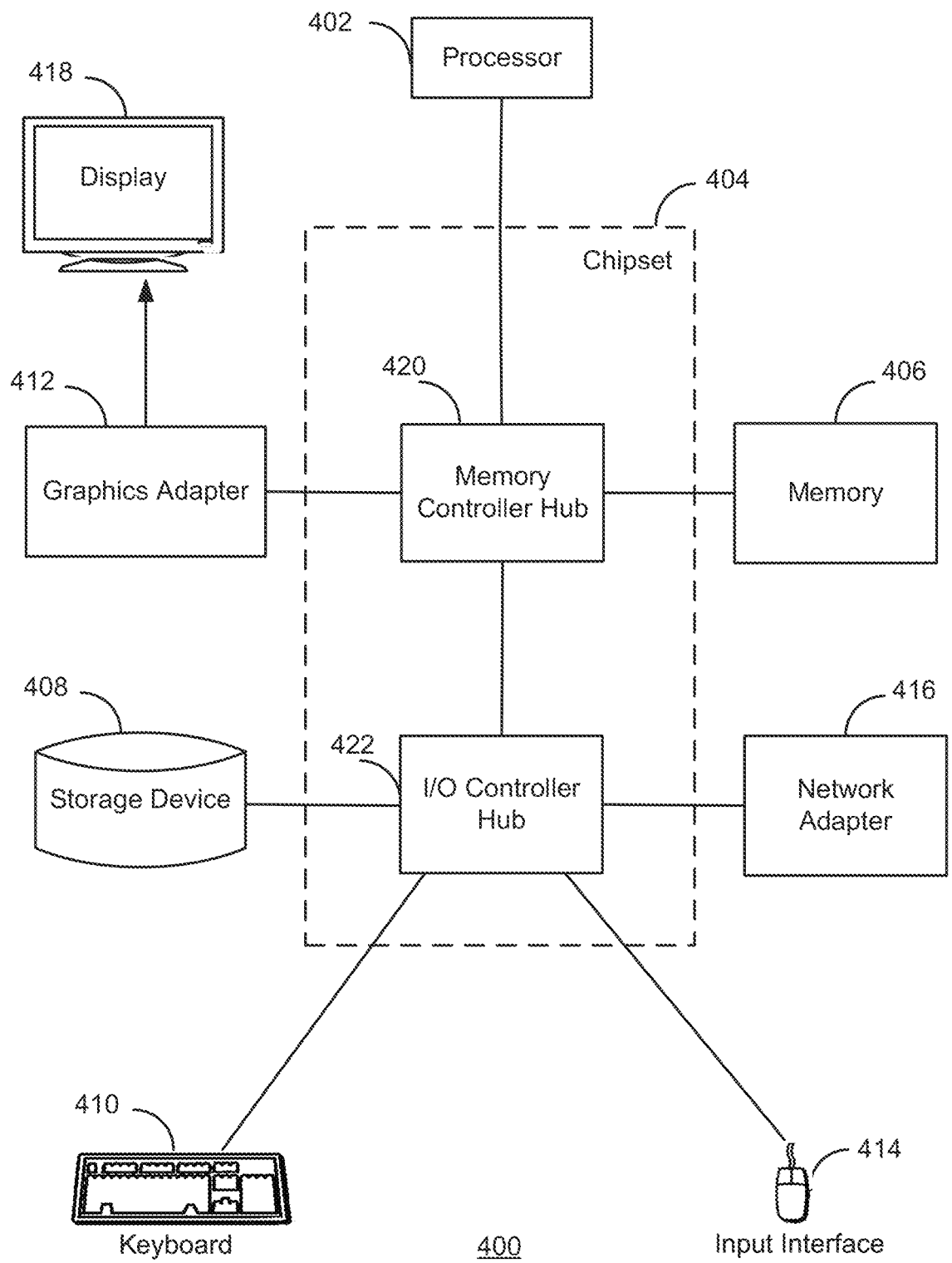
FIG. 4 is a schematic representation illustrating an exemplary computing device for implementing system and methods described in FIGS. 1A-1B, 2A-2B, and 3.

FIG. 4 illustrates an example computing device 400 for implementing system and methods described in FIGS. 1A-1B, 2A-2B, and 3. In some embodiments, the computing device 400 includes at least one processor 402 coupled to a chipset 404. The chipset 404 includes a memory controller hub 420 and an input/output (I/O) controller hub 422. A memory 406 and a graphics adapter 412 are coupled to the memory controller hub 420, and a display 418 is coupled to the graphics adapter 412. A storage device 408, an input interface 414, and network adapter 416 are coupled to the I/O controller hub 422. Other embodiments of the computing device 400 have different architectures.

The storage device 408 is a non-transitory computer-readable storage medium such as a hard drive, compact disk read-only memory (CD-ROM), DVD, or a solid-state memory device. The memory 406 holds instructions and data used by the processor 402. The input interface 414 is a touch-screen interface, a mouse, track ball, or other type of input interface, a keyboard, or some combination thereof, and is used to input data into the computing device 400. In some embodiments, the computing device 400 may be configured to receive input (e.g., commands) from the input interface 414 via gestures from the user. The graphics adapter 412 displays images and other information on the display 418. As an example, the display 418 can show visualizations of molecular interface. The network adapter 416 couples the computing device 400 to one or more computer networks.

The computing device 400 is adapted to execute computer program modules for providing functionality described herein. As used herein, the term "module" refers to computer program logic used to provide the specified functionality. Thus, a module can be implemented in hardware, firmware, and/or software. In one embodiment, program modules are stored on the storage device 408, loaded into the memory 406, and executed by the processor 402.

The types of computing devices 400 can vary from the embodiments described herein. For example, the computing device 400 can lack some of the components described above, such as graphics adapters 412, input interface 414, and displays 418. In some embodiments, a computing device 400 can include a processor 402 for executing instructions stored on a memory 406.

In various embodiments, the different entities depicted in FIGS. 1A and/or FIG. 1B may implement one or more computing devices to perform the methods described above. For example, the medical compliance system 130, third party entity 110A, and third party entity 110B may each employ one or more computing devices. As another example, one or more of the modules of the medical compliance system 130 (e.g., three dimensional model module 140, interface selection module 145, complex characterization module 150, and molecular interface store 155) may be implemented by one or more computing devices to perform the methods described above. As yet another example, one or more devices of the medical compliance system 130 (e.g., atomic model determination device 165 or therapeutic validation device 170) may employ one or more computing devices or may be communicatively coupled to one or more computing devices.

The methods for performing the interface analysis and/or methods for discovering new therapeutic candidate molecule can be implemented in hardware or software, or a combination of both. In one embodiment, a non-transitory machine-readable storage medium, such as one described above, is provided, the medium comprising a data storage material encoded with machine readable data which, when using a machine programmed with instructions for using said data, is capable of perform the methods disclosed herein including methods for performing the interface analysis and/or methods for discovering new drugs. Embodiments of the methods described above can be implemented in computer programs executing on programmable computers, comprising a processor, a data storage system (including volatile and non-volatile memory and/or storage elements), a graphics adapter, an input interface, a network adapter, at least one input device, and at least one output device. A display is coupled to the graphics adapter. Program code is applied to input data to perform the functions described above and generate output information. The output information is applied to one or more output devices, in known fashion. The computer can be, for example, a personal computer, microcomputer, or workstation of conventional design.

Each program can be implemented in a high level procedural or object oriented programming language to communicate with a computer system. However, the programs can be implemented in assembly or machine language, if desired. In any case, the language can be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system can also be considered to be implemented as a computer-readable storage medium, configured with a computer program, where the storage medium so configured causes a computer to operate in a specific and predefined manner to perform the functions described herein.

The signature patterns and databases thereof can be provided in a variety of media to facilitate their use. "Media" refers to a manufacture that contains the signature pattern information of the present invention. The databases of the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure can be chosen, based on the means used to access the stored information. A variety of data processor programs and formats can be used for storage, e.g., word processing text file, database format, etc.

EXAMPLES

The following Examples are merely illustrative and are not intended to limit the scope or content of the invention in any way.

Example 1: Development of a Predictive Model Useful for Populating Medical Compliance Forms This example describes the steps for training and implementing a predictive model useful for populating medical compliance forms (MCFs) for improving medical compliance and patient outcomes.

Generally, step 1 involves creating a dataset, such as a Health Lake dataset. Here, the first step to creating a custom model is to create an empty dataset that will eventually hold the training data for the model. At the time of creating the dataset, the type of classification performed by the custom model is selected. For example, types of classifications include clinical classification, clinical entity extraction, or clinical sentiment analysis.

Step 2 involves importing training items into the dataset. Here, the dataset is populated with a list of training content items labeled using the target categories. For example, the import_dataset function interface will take as input a .csv file that lists the locations of all training documents and the proper label for each training document. For the Patient Assessment Forms, progressnotes .csv will be used and uploaded to the storage. To generate labeled training content items, pre-trained natural language models are implemented to extract medical concepts and relationships from medical text. Proprietary clinical taxonomy databases are used to build relationship within the electronic medical records (EMRs) and map text from progress notes into a predefined set of medical knowledge categories. In production (for each clinic), the platform will allow creation of an extraction model trained using the clinic's Patient Assessment Forms, annotated medical text from the EMR and the relevant categories as defined in the form.

Step 3 involves training the machine learning model given the dataset of labeled training documents. For example, a custom model is created for classifying content. Such a custom model is trained using: a corpus of 50,000 de-identified clinical note dataset from the Beth Israel Deaconess Medical Center, clinical online databases such as Snomed CT, OpenEHR, EPIC on FHIR, security and & compliance. FHIR API, Oath 2 connection (EMR credential access), and pilot data including PAFs. The resulting model classifies the form type and patient record into models reflecting the various sections of the patient assessment form.

Step 4 involves evaluating the model following training by reviewing the model's precision, recall and F1 Score.

Step 5 involves deploying the model to production. For example, when the custom model meets quality standards, the models is deployed and used to make predictions request. Specifically, when the model is deployed, the model is used to classify novel content such as checking boxes on medical compliance forms (e.g., Patient Assessment Forms) based on EMR-Form comprehension.

Figure 5:
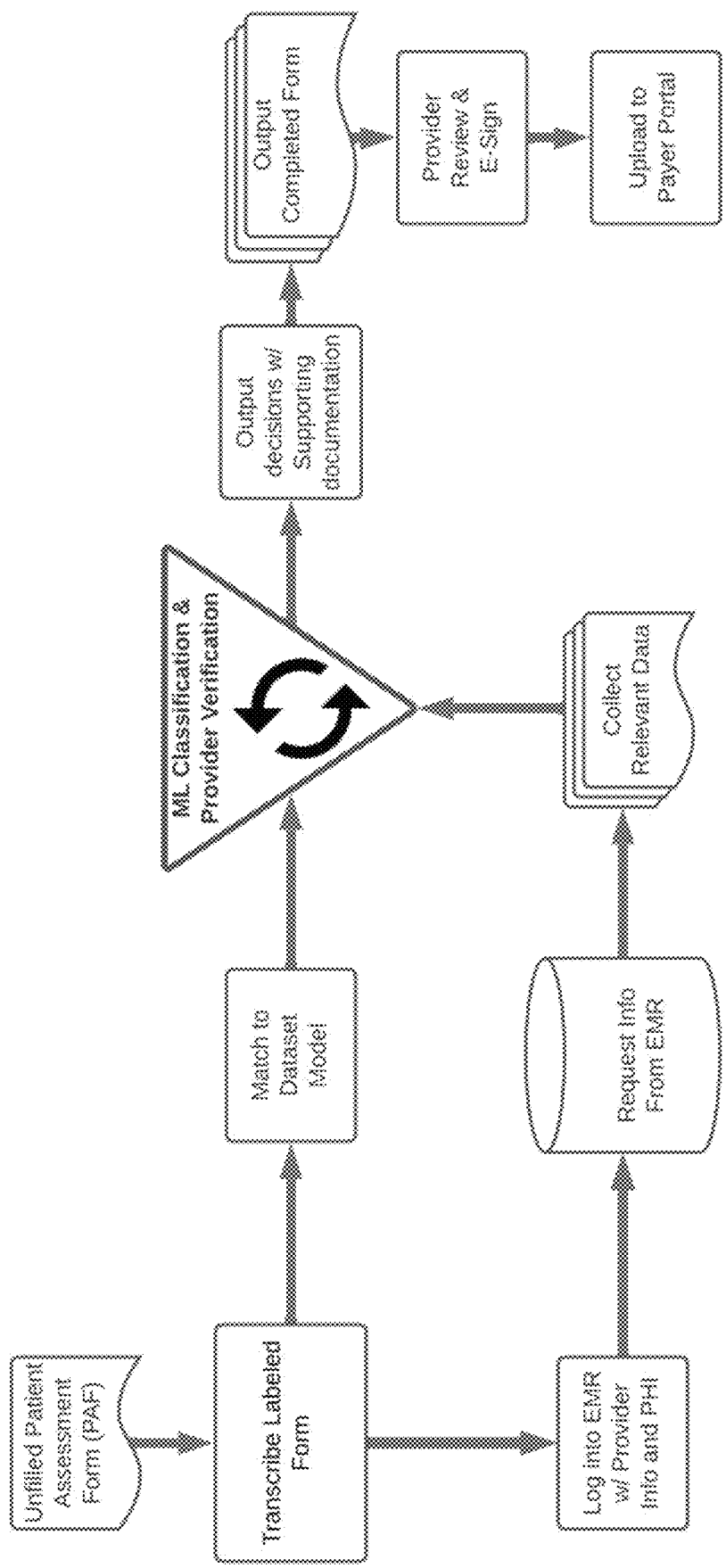
FIG. 5 is an example block diagram flow process for populating an unfilled patient assessment form (PAF) using machine learning classification, in accordance with a first embodiment.

Reference is now made to FIG. 5, which is an example block diagram flow process for populating an unfilled patient assessment form (PAF) using the deployed model, in accordance with a first embodiment. Here, the process begins with the unfilled PAF. The unfilled PAF is analyzed to determine the labeled form. For example, the unfilled PAF is analyzed to categorize the PAF according to a format of the PAF. Thus, the labeled form is matched to a previously trained model (e.g., indicated as a "dataset model") that can appropriately analyze the form according to its format. In parallel, as shown in FIG. 5, provider info is used to log into the electronic medical records (EMRs) and a request is sent to access patient data from the EMR. The relevant patient data is collected and the provided to the relevant predictive model.

The machine learning model analyzes both the form (e.g., one or more fields of the form) and the collected patient data and outputs decisions as to certain patient data that are to be included in the fields of the form. Additional supporting documentation can be generated, such as supporting documentation that backs the inclusion of certain data in the one or more fields. As a specific example, supporting documentation may support usage of one or more codes (e.g., billing codes) that are included in the fields.

Following the output decisions of the predictive model, the one or more fields of the form are populated with the patient data. Step 6 involves data augmentation and form output. The completed form is outputted and provided e.g., to a provider who will review the patient data included in the form. For example, a digital PDF is completed that is ready for approval by the provider before being uploaded to the payer portal. Medical text from various inputs such as patient assessment forms (PAFs) and electronic medical record (EMR) notes will be extracted. The extracted information include: patient and provider demographic as well as payer information, clinical taxonomy (medical concepts), such as medications, procedures, and medical conditions, functional features, such as temporal relationships, subjects, and certainty assessments/relations, such as HCC codes for risk adjustment factor (RAF) score accuracy and specificity.

Further details of these steps for training and implementing a predictive model for populating MCFs is described below.

1. Dataset Creation and Import

As a first step, training documents are collected and labeled. These training documents may represent a diverse set of training documents that reflects a range of documents that the predictive model is expected to handle. The preparation steps for training documents can differ depending on task predicted by the predictive model (e.g., tasks of clinical classification, clinical entity extraction, or clinical sentiment analysis). The training documents will represent the types of content that are to be classified. Thus, the training documents will be labeled with category labels and will serve as the input for training the predictive model.

To house the training documents, first, an empty dataset is created. The newly created dataset doesn't contain any data until training documents are imported into it. A Web UI is built and used to enable creation of the dataset. The main steps for building the dataset include: 1. Create a dataset resource, 2. Import healthcare/clinical training data into the dataset, 3. Label the healthcare documents/forms and/or identify the named entities. Regarding the importation of healthcare/clinical training data, raw data from the sources listed above (e.g., hospitals, clinical online databases such as Snomed CT, OpenEHR, EPIC, etc.) are run through a deidentification process in which patient identity information is split from the main set and stored on premises (e.g., at the hospital or in the clinical online database). Each patient is assigned a 10 digit Pin number (PDpin) that can only be traced back to the patient when on premises.

The script DI_optumCSV.py takes a batch input of Optum patient assessment forms and splits the input into three data sheets.

1. *ProviderInitials*_pts_PDpin.csv
2. *ProviderInitials*_pts_diagnosis_PDpin.csv
3. *ProviderInitials*_providerDets.csv The pts_PDpin contains the patient names and the 10 digit code. This is only stored on premises. The pts_diagnosis_PDpin contains the pertinent patient data: Condition, Suspect Detail, Disposition, Annual Care Visit Date, Provider Group ID, Line of Business, Contract ID, Incentive Program, PDpin. This data is streamed to the dataset for inclusion as training documents. ProviderDets .csv stores all provider specific information on premises as well.

2. Labeling Training Documents

To be useful for training a model, training documents in the dataset are labeled according to the objective/task of the predictive model. At this stage, the objective/task of the predictive model is selected. Example objectives include:

Single label classification assigns a single label to each classified document

Multi-label classification allows a document to be assigned multiple labels

Entity extraction identifies entities in documents

Clinical taxonomy analysis analyzes attitudes within documents

The quality of the training data strongly impacts the effectiveness of the predictive model. Labels for training documents can be provided in any of three ways:

Include labels in a .csv file (for classification and sentiment analysis only)

Label documents in the Natural Language UI

Request labeling from human labelers using a Platform Data Labeling Service

To label healthcare documents in the Natural Language UI, the Web Platform is connected to SQL RDS endpoint to visualize dataset listings and its details. Current technological specifications are as follows:

The display name of the selected dataset appears in the title bar, and the page lists the individual documents in the dataset along with their current labels.

The navigation bar along the left summarizes the number of labeled and unlabeled documents and enables filtering of the document list by label or sentiment value.

To assign labels or clinical sentiment values to unlabeled documents or change document labels, the documents that are to be updated are selected and the label(s) or value are assigned.

Following document scanning, individual fields will be identified with labels to define the type of medical/patient data needed to complete the field. The platform will search for accurate medical information to output. This allows for relevant medical documentation to be pulled that verifies and matches with content in the form. This also allows for supporting documentation to be compiled and outputted with the completed form ready for submission.

Figure 6:
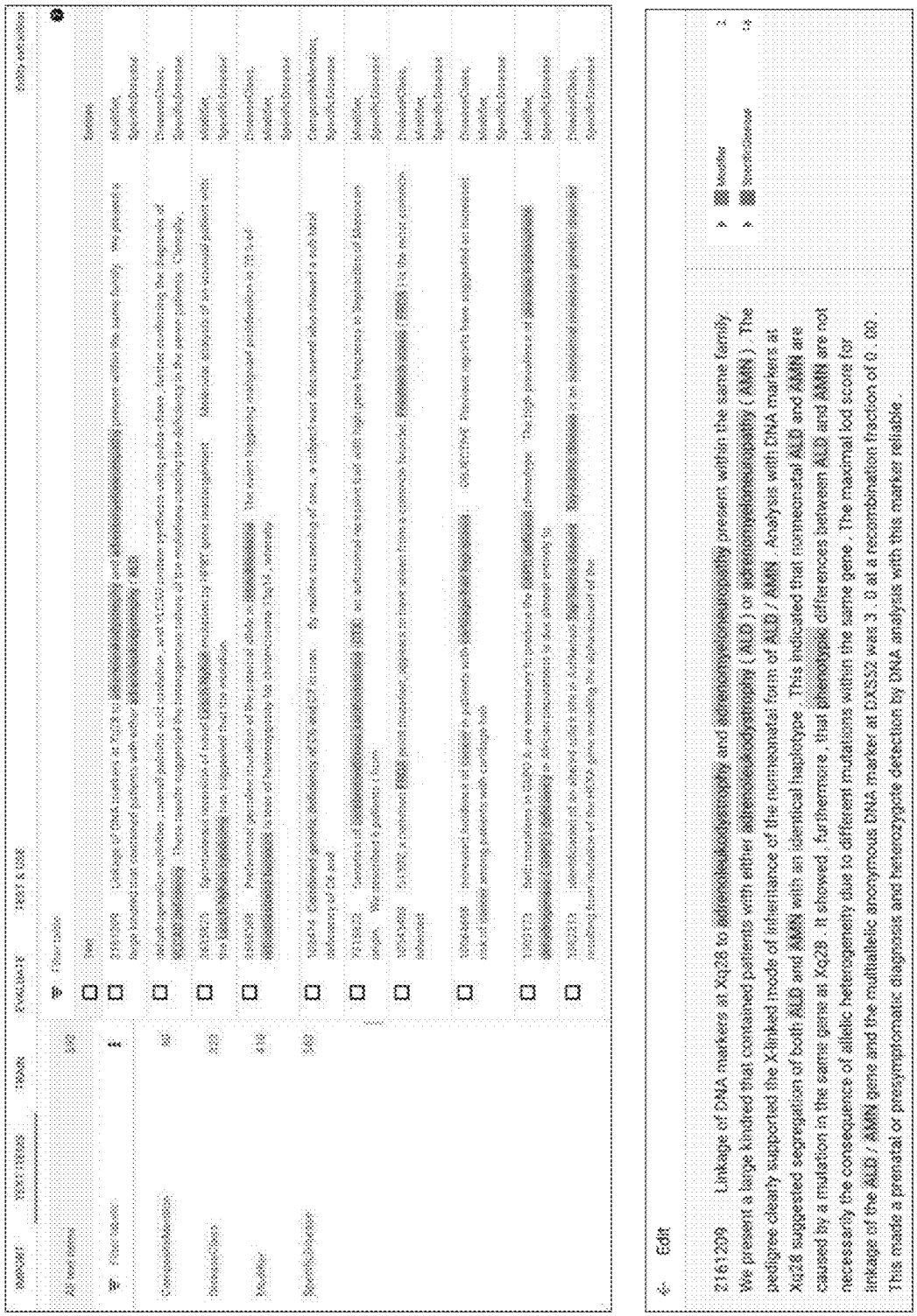
FIG. 6 shows example annotations and/or labeling of training documents. Such training documents are useful for training a predictive model.

FIG. 6 shows example annotations and/or labeling of training documents. Such training documents are useful for training a predictive model. To annotate fields of training documents, annotations can be added in the Natural Language Web UI. Specifically, within the Web UI, the dataset is selected from the dataset listing page to see its details. The display name of the selected dataset appears in the title bar, and the page lists the individual documents in the dataset along with any annotations in them. The navigation bar along the left summarizes the labels and the number of times each label appears. The document list can also be filtered by label.

3. Training a Predictive Model

Once given a dataset with a set of labeled training documents, the dataset is now used to train the predictive model. For example, the dataset is used to train the predictive model to populate a patient assessment form. Training a model can take several hours to complete. The required training time depends on several factors, such as the size of the dataset, the nature of the training items, and the complexity of the models.

In particular, a particular extraction is performed which provides context-sensitive data extraction that is field and position-specific to accelerate training of the predictive model. Specifically, representative samples of the type of medical text that is to be analyzed is provided. The representative samples are annotated with labels that identify the types of entities that the predictive model is to identify.

Specifically, between 20 and 1,000,000 samples (e.g., between 50 and 100,000) of training documents (e.g., patient assessment forms and de-identified medical data) are supplied to train the predictive model. Documents can be in text, PDF, TIFF, or image format, or compressed into a ZIP file. The documents are labeled with between one and 5000 unique labels (e.g., between 2 and 100 unique labels) to annotate the entities that the model is to learn to extract. Label names can be between two and 30 characters. Each label can annotate between one and 10 words, and each label can be applied to at least 10 different documents. As an example, to train a model effectively, the training data set should use each label at least 200 times.

Training documents can be varied to ensure that the predictive model can handle a wide range of documents. For example, training documents can include different lengths (e.g., between 1 page and up to hundreds of pages), different documents authored by different insurance companies, different formats, different wordings, different styles, and so on. When using multi-label classification, all relevant labels are applied to each document. For example, if documents provide details about patient assessments, then there can be labels for both preventative screening and progress notes. If a document includes both types of information, both labels are applied.

At least 10 documents per label is preferred for training the predictive model. However, the confidence scores from the predictive model can be further improved by using more examples per label. Better confidence scores are especially helpful when the model returns multiple labels when it classifies a document. The model is trained using at least 50 examples per label and is further evaluated. Additional examples are incorporated and the predictive model is retrained until the performance meets accuracy targets, which sometimes may be achieved at hundreds or even 1000 examples per label. In particular scenarios, the predictive model is trained using training data with at most 100 times more documents for the most common label than for the least common label. Additionally, the very low frequency labels are removed.

The training documents can be further formatted. For example, training data is uploaded to Natural Language as JSONL files that contain the sample text and documents. Each line in the file is a single training document, specified in one of the following forms:

The full content of the document (I.e. EMR+PAF), between 10 and 10000 bytes long (UTF-8 encoded)

The URL of a the deidentified data export CSV file from a Cloud Storage bucket associated with a project Additionally, a "None_of_the_above" label is implemented for documents that don't match any of the defined labels. For example, if labeled documents originate from Optum and United Healthcare, but the dataset contains documents about other payers, such as Wellmed or Devoted, then the documents from other payers can be labeled as "None_of_the_above". Without such a label, the trained model may attempt to assign all documents to one of the defined labels, even documents for which those labels are unsuitable.

The "None_of_the_above" label can be useful in the following scenario: suppose the long-term plan is to train a model that classifies patient assessment form documents based on their document type (PAF, HQPAF, Attestation, policy document, and so on). There are thousands of document types, but for testing purposes, the model is trained with only 100 Patient Assessment Form types, with plans to train more comprehensive models in the future. During this early stage, most documents sent for classification will be "out of domain" for the initial label set; that is, they are document types outside of the initial 100 types. If the predictive model is trained using only the initial 100 labels, the predictive model will attempt to classify the "out of domain" documents using one of the existing labels, thereby reducing the accuracy of the predictive model.

Thus, in such scenarios, two models can be trained:
1) ParaDocs Clinical Classification Model: This model classifies forms/documents into the current set of labels
2) ParaDocs Document Filtering Model: This model predicts whether a form/document fits within the current set of labels or is "out of domain"

Thus, each document is first submitted to the clinical filtering model, and only "in domain" documents are then provided to the classification model. The filtering model makes a binary prediction about whether a document belongs to any of the 100 types (e.g., labels), and then the classification model identifies the type of document.

To train a predictive model, the training data is randomly divided into the three sets:
- 80% of documents are used for training
- 10% of documents are used for validation (hyper-parameter tuning and/or to decide when to stop training)
- 10% of documents are reserved for testing (not used during training)

If document in the training data are to be specified in one of training, validation, or testing, documents can be explicitly assigned in the CSV file as described below. Specifically, a CSV file is created that lists all training documents. The CSV file can have any filename, can be UTF-8 encoded, and ends with a .csv extension. It is stored in the Storage bucket associated with the project. The CSV file has one row for each training document, with these columns in each row: 1. Which set to assign the content in this row to:

TRAIN—Document is used to train the model.
VALIDATION—Document is used to validate the results that the model returns during training.
TEST—Document is used to verify the model's results after the model has been trained.

If values are included in this column to specify one of training, validation, and testing, at least 5% of training data is to be included for each category.

Alternatively, if documents are not to be explicitly assigned, Natural Language automatically divides the documents into three sets, using approximately 80% of the data for training, 10% for validation, and 10% for testing (up to 10,000 pairs for validation and testing).

For clinical classification and clinical sentiment analysis, the document can be a text file, PDF file, TIFF file, image file or ZIP file; for entity extraction, it is a JSONL file. For clinical classification and clinical sentiment analysis, the value in this column can be quoted in-line text rather than a Storage URI. For clinical classification datasets, a comma-separated list of labels is optionally included that identifies how the document/form is categorized. Labels start with a letter and only contain letters, numbers, and underscores. Up to 20 labels for each document is included.

For clinical sentiment analysis datasets, optionally included is an integer indicating the sentiment value for the content. The sentiment value ranges from 0 (strongly negative) to a maximum value of 10 (strongly positive).

4. Clinical Taxonomy Analysis

Figure 7:
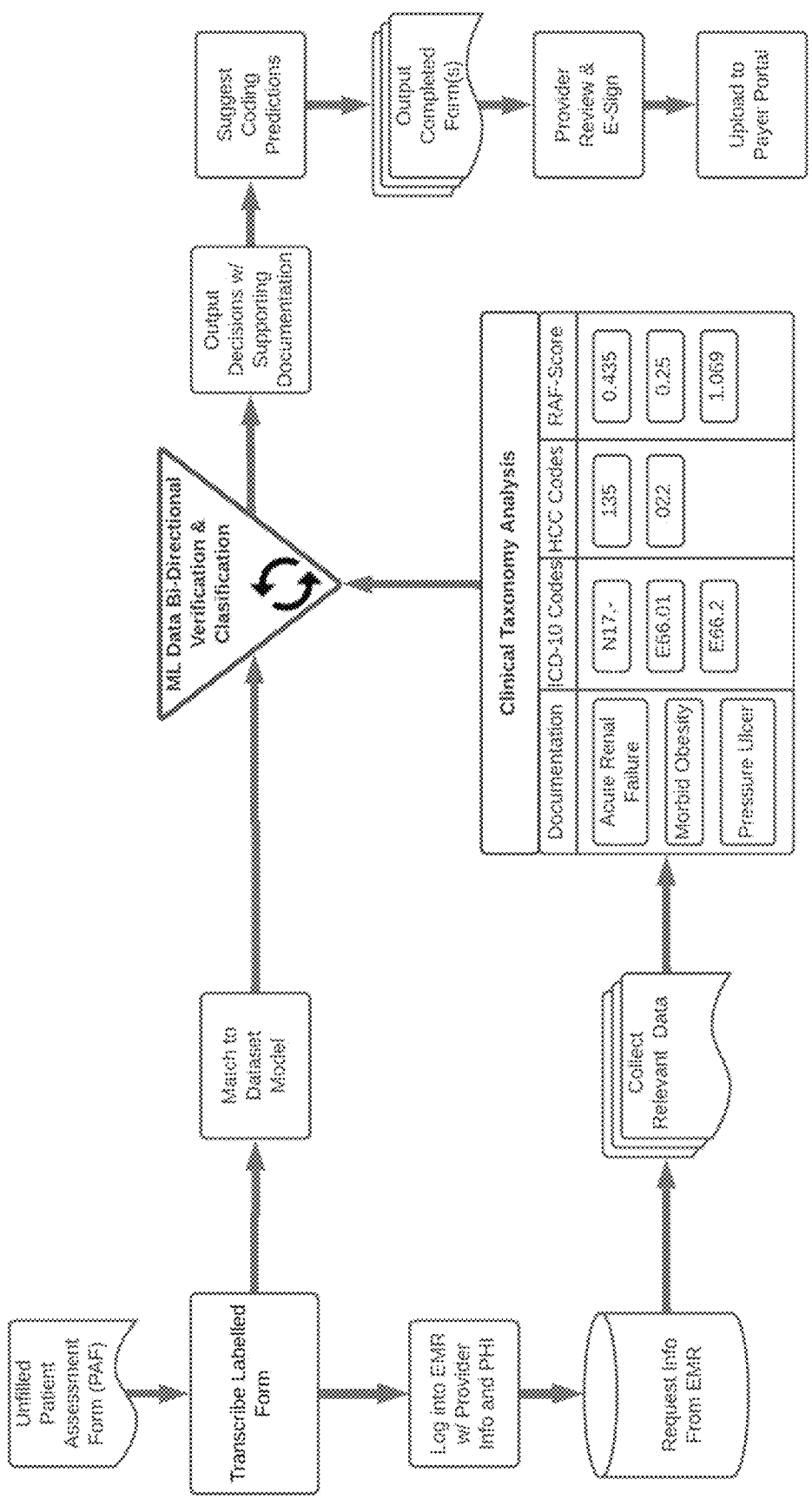
FIG. 7 is an example block diagram flow process for populating an unfilled patient assessment form (PAF) using machine learning classification, in accordance with a second embodiment.

FIG. 7 is an example block diagram flow process for populating an unfilled patient assessment form (PAF) using machine learning classification, in accordance with a second embodiment. Here, FIG. 7 shows the inclusion of clinical taxonomy analysis which provides further context for the machine learned implementation of the predictive model. Data extracted from the EMR and medical compliance forms develop relations based on the hierarchy of clinical data. Clinical taxonomy databases provide structured clinical data, improving clinical sentiment accuracy for predictive models, thereby providing the ability to search for supporting documentation to reference additional information that may be valuable (e.g., a suggested billing code). In addition, bi-directional data input comparison greatly increases the accuracy of our features.

Of note, the clinical taxonomy analysis includes various information such as documentation, codes (e.g., ICD-10 codes, HCC codes), and scores (e.g., risk adjustment factor (RAF) score or HEDIS score). Thus, the clinical taxonomy analysis is useful for predicting optimal codes based on relevant medical documentation of patients. In some scenarios, the clinical taxonomy analysis can be implemented in an interface, such as a user interface (UI). The UI for a user (e.g., provider) will be as a dashboard with all analytics and suggestions. Hovering over completed tasks shows accompanied sources of information gathered by the EMR to suggest a code. This code will be highlighted along with the corresponding RAF or HEDIS score.

5. Model Evaluation & Prediction

After training a predictive model, Natural Language uses documents from the set aside test set to evaluate the quality and accuracy of the trained model. Natural Language provides an aggregate set of evaluation metrics indicating how well the model performs overall, as well as evaluation metrics for each category label, indicating how well the model performs for that label.

Precision and recall measure how well the model is capturing information, and how much it is leaving out. Precision indicates, from all the documents identified as a particular entity or label, how many actually were supposed to be assigned to that entity or label. Recall indicates, from all the documents that should have been identified as a particular entity or label, how many were actually assigned to that entity or label.

The Confusion matrix (Only present for single-label-per-document models) represents the percentage of times each label was predicted in the training set during evaluation. Ideally, label one would be assigned only to documents classified as label one, etc. Natural Language creates the confusion matrix for up to 10 labels. If more than 10 labels, the matrix includes the 10 labels with the most confusion (incorrect predictions).

For sentiment predictive models, performance can be measured according to mean absolute error (MAE) and mean squared error (MSE) which measure the distance between the predicted sentiment value and the actual sentiment value. Lower values indicate more accurate models. Linear-weighted kappa and quadratic-weighted kappa measure how closely the sentiment values assigned by the model agree with values assigned by human raters. Higher values indicate more accurate models.

In general, the disclosed metrics are used to evaluate the readiness of the predictive model. Low precision and recall scores can indicate that the model requires additional training data or has inconsistent annotations. Perfect precision and recall can indicate that the data is too easy and may not generalize well. Predictive models that do not satisfy the requisite performance metrics can undergo further training to improve the performance. For example, additional training documents can be incorporated, different labels can be added, different types of training documents can be incorporated (e.g., longer or shorter documents, documents with different formats, documents using different wording, documents with different styles).

Following training (e.g., training a model that exhibits sufficient predictive accuracy), the predictive model can be deployed. A prediction occurs when a document (e.g., a medical compliance form) is submitted to the predictive model. The predictive model analyzes the document according to the objective for that model (named entity recognition, classification, or clinical taxonomy analysis), and outputs decisions as to patient data that are to be populated in one or more fields of the document.

Although the description above refers to a single document, Natural Language can support both online prediction, where a single document is provided and the model returns the analysis synchronously, as well as batch prediction, where a collection of documents is provided and the model analyzes asynchronously.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method for improving medical compliance, the method comprising:
    generating a de-identified training dataset, wherein the de-identified training dataset is generated by:
        obtaining de-identified electronic medical record (EMR) data comprising patient data and patient identifiers; and
        generating training medical compliance forms (MCFs) including portions of the patient data from the de-identified EMR data, wherein the training MCFs include fields for which one or more labels have been assigned;
    training a predictive model with the de-identified training dataset;
    obtaining an unfilled medical compliance form (MCF);
    identifying one or more fields of the unfilled medical compliance form for populating health data of a patient;
    transmitting a patient identifier to an entity, wherein the entity has a first dataset that includes patient identifiers and corresponding patient identities and a second dataset that includes patient identifiers and corresponding patient data;
    receiving, from the second dataset of the entity, the corresponding patient data of the patient without receiving the identity of the patient; deploying the predictive model to analyze the one or more fields;
    wherein the predictive model is agnostic to the patient identity and:
        assesses one or more guided paths of a clinical taxonomy database to an output decision and contextual characteristics of the one or more fields; and
        selects an output decision of a plurality of output decisions according to the one or more guided paths, wherein the output decision identifies subsets of patient data received from the entity to be included in the one or more fields;
    populating the one or more fields of the unfilled MCF with the identified subsets of the patient data to generate a populated MCF for the patient; and
    providing the populated MCF.

2. The method of claim 1, wherein the clinical taxonomy include medical codes correlated to diagnosis and HEDIS scores.

3. The method of claim 1, wherein the model further generates the one or more guided paths based on a history of the patient.

4. The method of claim 1, wherein generating the one or more guided paths further comprises generating one or more output decisions for a first, second, and third level of output decisions.

5. The method of claim 1, wherein generating the one or more guided paths comprises generating a path that maximizes a HEDIS score.

6. The method of claim 1, wherein the output decision further comprises a suggested medical categorization for inclusion in the one or more fields.

7. The method of claim 6, wherein the suggested medical categorization includes an ICD-10 code.

8. The method of claim 3, wherein generating the one or more guided paths to an output decision comprises generating a risk adjustment factor score (RAF) for the output decision.

9. The method of claim 8, wherein the RAF score reflects a predicted cost for the patient if a code of the output decision is used.

10. The method of claim 1, wherein the method improves medical reporting compliance in comparison to Risk Adjustment Data Validation RADV audits.

11. A non-transitory computer readable medium comprising instructions that, when executed by a processor, cause the processor to:
    generate a de-identified training dataset, wherein the de-identified training dataset is generated by a by:
        obtaining de-identified electronic medical record (EMR) data comprising patient data and patient identifiers; and
        generating training medical compliance forms (MCFs) including portions of the patient data from the de-identified EMR data, wherein the training MCFs include fields for which one or more labels have been assigned;
    train a predictive model with the de-identified training dataset;
    obtain an unfilled medical compliance form (MCF);
    identify one or more fields for populating health data of a patient of the unfilled medical compliance form;
    transmit the patient identifier to an entity, wherein the entity has a first dataset that includes patient identifiers and corresponding patient identities and a second dataset that includes patient identifiers and corresponding patient data;
    receive, from the second database of the entity, the corresponding patient data of the patient without receiving the identity of the patient; deploy the predictive model to analyze the one or more fields;
    wherein the predictive model is agnostic to the patient identity and:
        assesses one or more guided paths of a clinical taxonomy database to an output decision; and
        selects an output decision of a plurality of output decisions according to the one or more guided paths, wherein the output decision identifies subsets of patient data received from the entity to be included in the one or more fields; and
    populate the one or more fields of the unfilled MCF with the identified subsets of the patient data to generate a populated MCF for the patient; and
    provide the populated MCF.

12. The non-transitory computer readable medium of claim 11, wherein the clinical taxonomy database includes medical codes correlated to diagnosis and HEDIS scores.

13. The non-transitory computer readable medium of claim 11, wherein the predictive model is configured to generate the one or more guided paths based on a history of the patient.

14. The non-transitory computer readable medium of claim 11, wherein the processor is configured to generate one or more output decisions for a first, second, and third level of output decisions.

15. The non-transitory computer readable medium of claim 11, wherein the processor is configured to generate the one or more guided paths to maximize a HEDIS score.

16. The non-transitory computer readable medium of claim 11, wherein the processor is configured to provide a suggested medical categorization for inclusion in the one or more fields.

17. The non-transitory computer readable medium of claim 16, wherein the suggested medical categorization includes an ICD-10 code.

18. The non-transitory computer readable medium of claim 11, wherein the processor is configured to generate a risk adjustment factor score (RAF) for the output decision.

19. The non-transitory computer readable medium of claim 18, wherein the RAF score reflects a predicted cost for the patient if a code of the output decision is used.

20. The non-transitory computer readable medium of claim 11, wherein the non-transitory computer readable medium improves medical reporting compliance in comparison to Risk Adjustment Data Validation (RADV) audits.

* * * * *